United States Patent
Kawaura et al.

(10) Patent No.: US 8,241,323 B2
(45) Date of Patent: Aug. 14, 2012

(54) TISSUE CLOSING DEVICE

(75) Inventors: Masakatsu Kawaura, Ashigarakamigun (JP); Tomoji Maruyama, Ashigarakamigun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 810 days.

(21) Appl. No.: 11/850,327

(22) Filed: Sep. 5, 2007

(65) Prior Publication Data

US 2008/0065121 A1 Mar. 13, 2008

(30) Foreign Application Priority Data

Sep. 7, 2006 (JP) .................................. 2006-243291

(51) Int. Cl.
*A61B 17/08* (2006.01)
(52) U.S. Cl. ........................................ 606/213; 606/139
(58) Field of Classification Search .................. 128/887; 604/514; 606/146, 194, 213, 215, 216, 232, 606/139
See application file for complete search history.

(56) References Cited

U.S. PATENT DOCUMENTS

| | | | | |
|---|---|---|---|---|
| 373,372 | A * | 11/1887 | King | 606/146 |
| 5,021,059 | A * | 6/1991 | Kensey et al. | 606/213 |
| 5,441,517 | A | 8/1995 | Kensey et al. | |
| 5,545,178 | A * | 8/1996 | Kensey et al. | 606/213 |
| 5,667,513 | A * | 9/1997 | Torrie et al. | 606/104 |
| 5,814,073 | A * | 9/1998 | Bonutti | 606/232 |
| 6,613,070 | B2 * | 9/2003 | Redmond et al. | 606/213 |
| 7,597,705 | B2 * | 10/2009 | Forsberg et al. | 606/213 |
| 2001/0003158 | A1 * | 6/2001 | Kensey et al. | 606/213 |
| 2005/0085852 | A1 * | 4/2005 | Ditter | 606/213 |
| 2006/0004409 | A1 * | 1/2006 | Nobis et al. | 606/232 |

FOREIGN PATENT DOCUMENTS

| | | |
|---|---|---|
| JP | 5-508563 A | 12/1993 |
| JP | 9-512461 A | 12/1997 |
| WO | 95/29635 A1 | 11/1995 |

OTHER PUBLICATIONS http://www.thefreedictionary.com/foam Nov. 8, 2011.*
http://www.thefreedictionary.com/Latching Nov. 8, 2011.*

* cited by examiner

*Primary Examiner* — Kathleen Sonnett
*Assistant Examiner* — David Eastwood
(74) *Attorney, Agent, or Firm* — Buchanan Ingersoll & Rooney PC

(57) ABSTRACT

A tissue closing device for closing an opening penetrating a tissue membrane in a living body includes a closure configured to close the opening and a device configured to deploy the closure. The closure includes a seal portion and a deformation portion for covering the opening and tissue membrane surrounding the opening from opposite sides, and a connecting portion connecting the seal portion and the deformation portion. The arrangement device includes a storing member for storing the deformation portion and supporting the connecting member, and a hand-operated portion on the proximal side of the storing member. The storing member includes a take-out port which is openable from a closed state. The deformation portion is discharged exterior of the storing member by opening the take-out port.

24 Claims, 19 Drawing Sheets (a) Cross-section along line d-d (b) Cross-section along line e-e (c) Cross-section along line f-f

TISSUE CLOSING DEVICE

TECHNICAL FIELD

The disclosed subject matter generally pertains to a device used to close a puncture hole in a living being. More specifically, the subject matter relates to a living body tissue closure and a living body tissue closing device for closing an opening penetrating tissue membrane of a living body.

BACKGROUND DISCUSSION

Low-invasion operations carried out by inserting a device for diagnosis or treatment, such as a catheter, into a blood vessel or some other tissue are known and performed on a quite often basis. For example, to treat a constriction of the coronary artery of the heart, it is necessary to insert a device such as a catheter into a blood vessel in order to perform therapeutic treatment on the constriction.

This insertion of an instrument such as a catheter into a blood vessel is normally performed through a puncture formed by dissecting or puncturing the femoral region. After the therapeutic treatment is completed, it is necessary to perform a stanching operation to stop the bleeding through the puncture. However, since the blood pressure upon bleeding (bleeding blood pressure) from the femoral artery is relatively high, it is oftentimes necessary for a person involved in the medical procedure to use a finger of their hand to press down on the site for a relatively long period of time.

In recent years, to stop bleeding more readily and with greater certainty, a variety of devices have been developed which are adapted to be inserted through a puncture hole to close a penetrated opening formed in a blood vessel. For example, U.S. Pat. No. 5,441,517 discloses a puncture closure device which is adapted to be inserted into an introducer sheath. In the device, a filament is held by a ball pressed by a spring at the proximal end of the device, and, when the device is drawn out, the filament slips while retaining a constant tension, whereby the device is drawn out. Finally, in the condition where an anchor portion is disposed at the position of a puncture hole formed in the blood vessel wall, while the filament is pulled, a collagen plug is pushed and compressed by a tamper, whereby the plug is collapsed. In this manner, the hole formed in the blood vessel wall is closed with a closure.

However, the anchor of this puncture closure device is liable to be swung in the front-rear direction and/or the left-right direction and turned about the longitudinal axis, with the result that the posture of the anchor is not very stable. Also, this puncture closure device cannot be used with an introducer sheath left indwelling after a procedure such as therapeutic treatment (e.g., Percutaneous Coronary Intervention: PCI) or after a diagnosis (e.g., Coronary AngioGraphy: CAG) is performed using a catheter which is directly used as the above-mentioned introducer sheath, since the distal end of the sheath is located in the deep site of the blood vessel. Therefore, the sheath left indwelling after the procedure cannot be used as the introducer sheath and so it is necessary to evulse or remove the indwelling sheath and then insert a new sheath for this exclusive use until the distal end is positioned in close contact with the blood vessel wall. Such procedure takes labor and time.

SUMMARY

According to one aspect, a tissue closing device for closing an opening penetrating a tissue membrane in a living body comprises a closure configured to close the opening and an arrangement device detachably retaining the closure to arrange the closure in the living body. The closure includes a seal portion for covering the opening and tissue membrane surrounding the opening from one side of the tissue membrane, a deformable deformation portion and a connecting portion connecting the seal portion and the deformation portion. The arrangement device includes a storing member and a hand-operated portion provided on the proximal side of the storing member. The storing member includes a storing portion and a supporting portion, with the storing member being configured for passage through the opening, and the support portion being located on the distal side of the storing portion and supporting the connecting portion at a region between the deformation portion and the seal portion. The closure is retained by the arrangement device so that the deformation portion is stored in the storing portion and the seal portion is located on the distal side relative to the support portion. The support portion is provided with a take-out port configured to be opened from a closed state. The support portion supports the connecting portion so that the seal portion is pivotally turnable in a single plane around a predetermined one of three mutually orthogonal axes relative to the storing portion when the take-out port is in the closed state, with the deformation portion being discharged exterior of the storing member by opening of the take-out port.

Another aspect involves a method of deploying a closure to close an opening penetrating a tissue membrane in a living body, wherein the closure includes a seal portion, a deformable deformation portion and a connecting portion connecting the seal portion and the deformation portion, with the deformation portion being stored within a storing portion of a storing member positioned at a distal side of a hand-operated portion, and the storing member also including a closed take-out port through which the connecting portion passes. The method involves positioning a distal end portion of the storing member so that the distal end portion of the storing member passes through the opening penetrating the tissue membrane in the living body, with the seal portion positioned on one side of the tissue membrane, moving the hand-operated portion in a proximal direction away from the opening to move the seal member to a position covering the opening and the tissue membrane surrounding the opening from the one side of the tissue membrane, continuing to move the hand-operated portion in the proximal direction to open the closed take-out port and discharge the deformation portion of the closure from the storing member, and further moving the hand-operated portion to deform the deformation portion so that the deformed deformation portion covers the opening and the tissue membrane surrounding the opening from the side of the tissue membrane opposite the one side.

BRIEF DESCRIPTION OF THE DRAWING FIGURES

Figure 1:
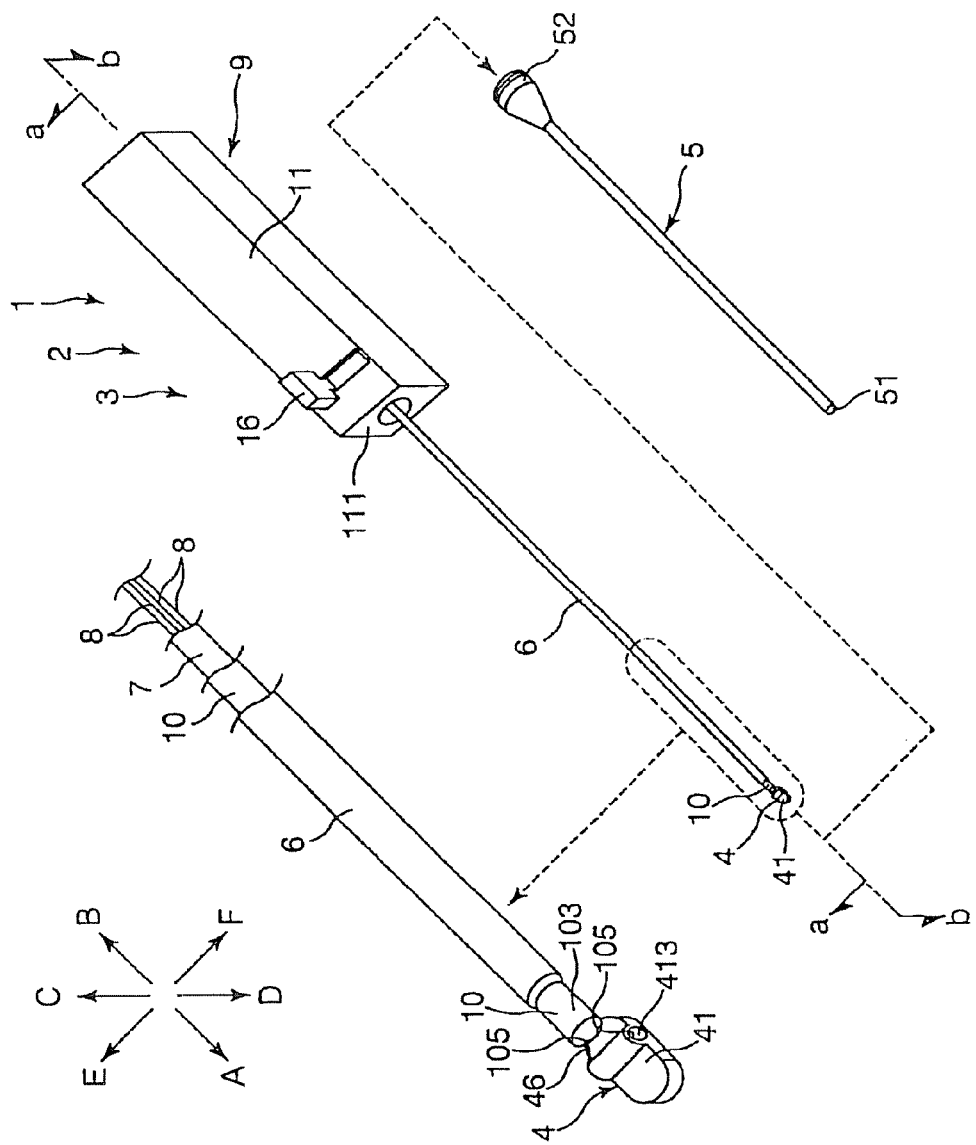
FIG. 1 is a perspective exploded view of an embodiment of the tissue closing device disclosed herein.

FIGS. 5(a) and 5(b) are views, partially in cross-section, of a hand-operated portion of the tissue closing device shown in FIG. 1, in which FIG. 5(a) is a side view showing the inside of the hand-operated portion, and FIG. 5(b) is a plan view showing the inside of the hand-operated portion.

FIGS. 6(a) and 6(b) are views of the hand-operated portion of the tissue closing device shown in FIG. 1, in which FIG. 6(a) is a cross-sectional view taken along the section line a-a of FIG. 1, and FIG. 6(b) is a cross-sectional view taken along the section line b-b of FIG. 1.

FIGS. 7(a) and 7(b) are views of the proximal portion side of the hand-operated portion of the tissue closing device shown in FIG. 1, in which FIG. 7(a) is a cross-sectional view taken along section line a-a of FIG. 1, and FIG. 7(b) is a cross-sectional view taken along the section line b-b of FIG. 1.

Figure 8:
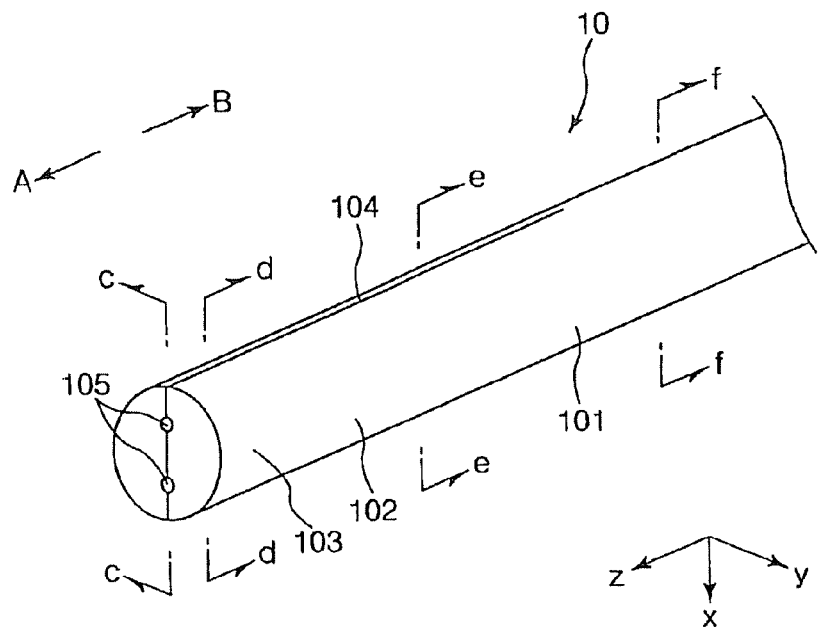

FIG. 8 is a perspective view of a slit tube of the tissue closing device shown in FIG. 1.

Figure 9:
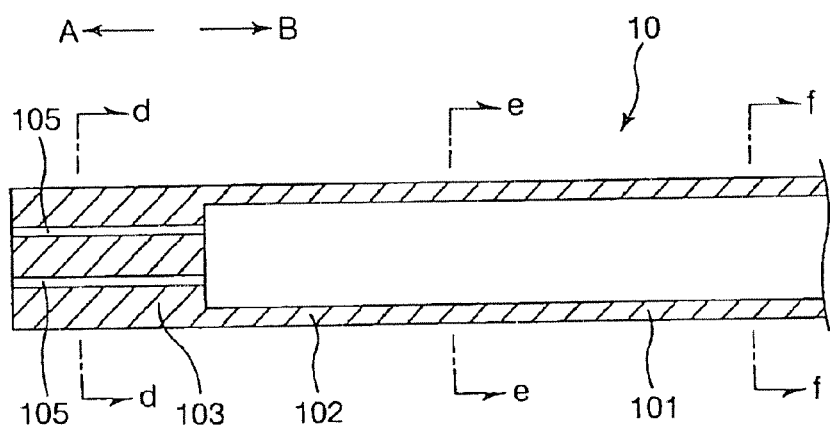

FIG. 9 is a cross-sectional view of the slit tube shown in FIG. 8 taken along the section line c-c in FIG. 8.

Figure 10:
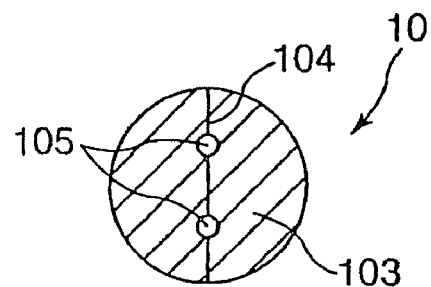
Figure 10:
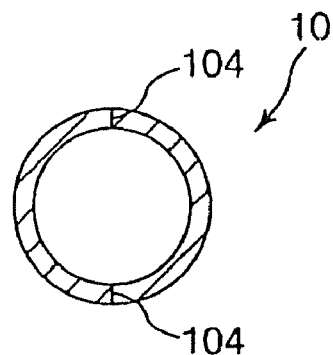
Figure 10:
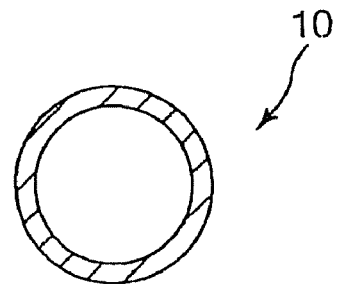

FIGS. 10(a), 10(b) and 10(c) are cross-sectional views of the slit tube shown in FIG. 8, in which FIG. 10(a) is a cross-sectional view taken along the section line d-d in FIGS. 8 and 9, FIG. 10(b) is a cross-sectional view taken along the section line e-e in FIGS. 8 and 9, and FIG. 10(c) is a cross-sectional view taken along the section line f-f in FIGS. 8 and 9.

Figure 11:
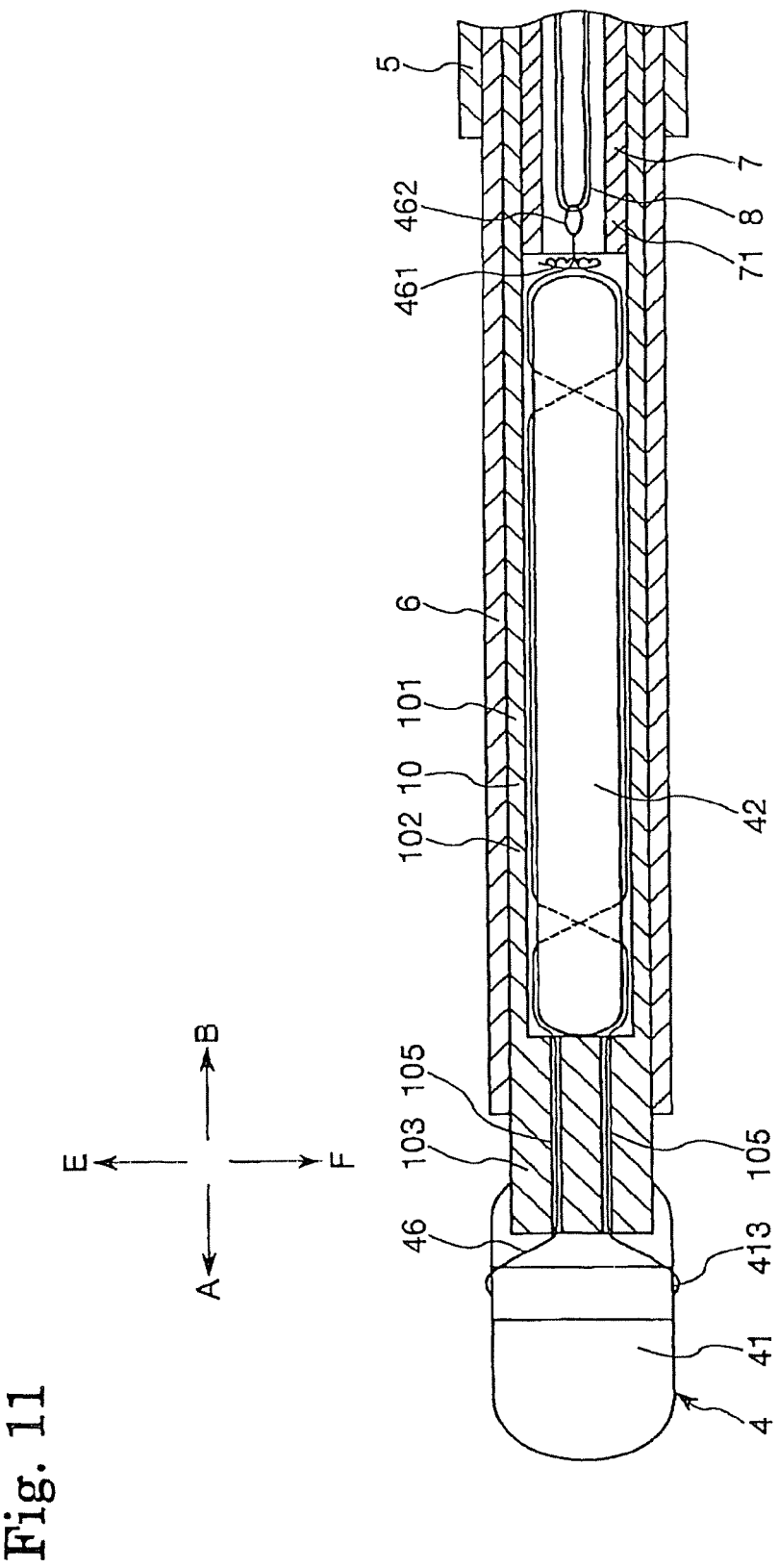

FIG. 11 is a longitudinal cross-sectional view of the distal portion side of the tissue closing device shown in FIG. 1.

FIGS. 12(a) and 12(b) are perspective views illustrating an operation (motion) of the tissue closing device shown in FIG. 1, in which FIG. 12(a) is an overall view, and FIG. 12(b) is a view showing the distal portion side.

Figure 13:
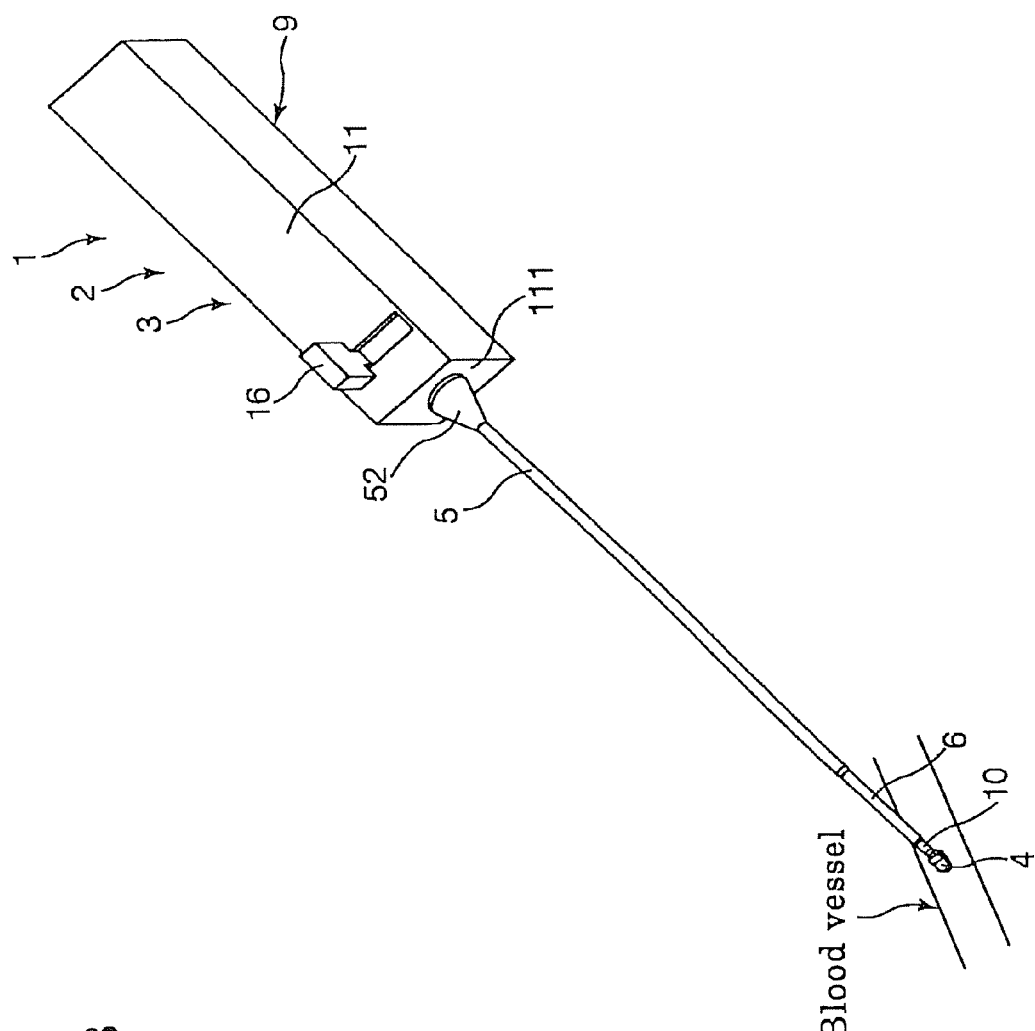

FIG. 13 is a perspective view illustrating additional operation (motion) of the tissue closing device shown in FIG. 1.

Figure 14:
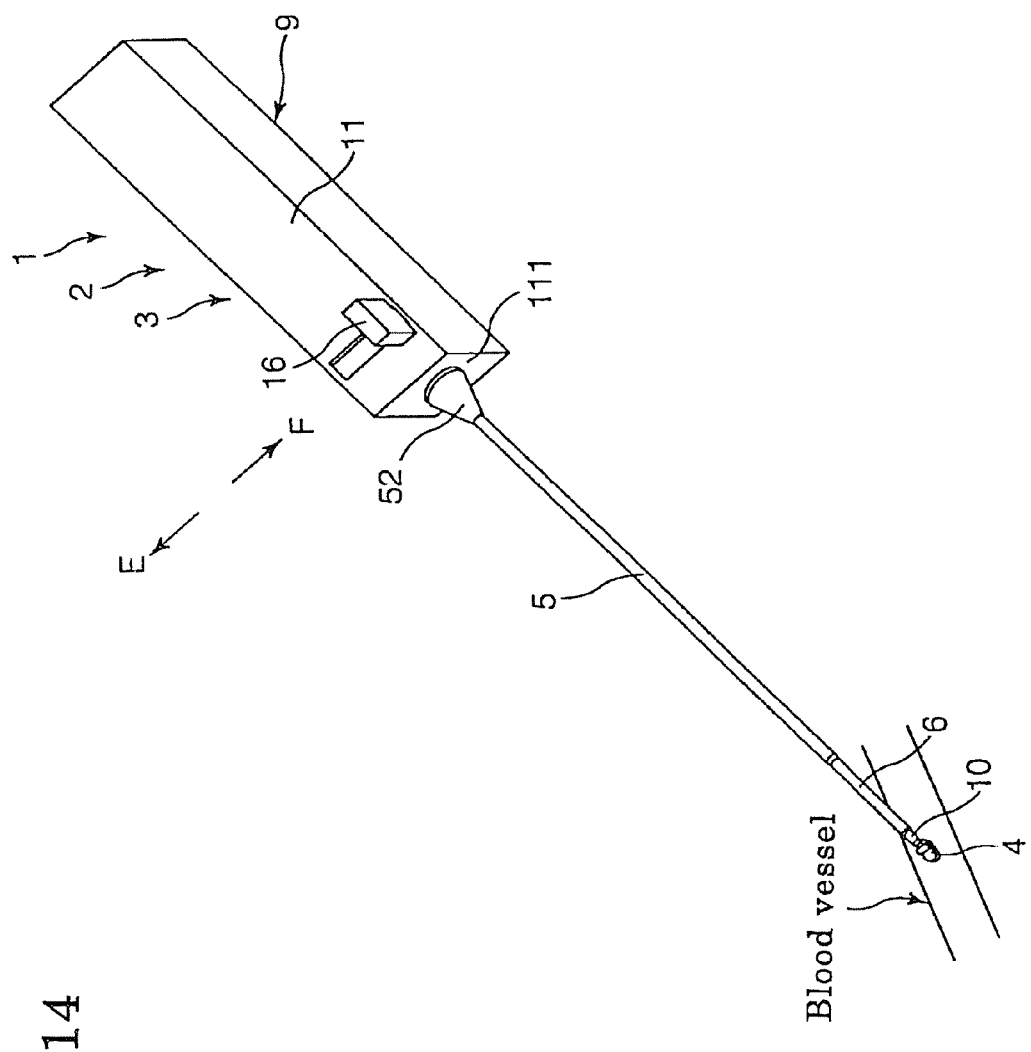

FIG. 14 is a perspective view illustrating additional operation (motion) of the tissue closing device shown in FIG. 1.

FIGS. 15(a) and 15(b) are perspective views illustrating additional operational aspects of the tissue closing device shown in FIG. 1, in which FIG. 15(a) is an overall view, and FIG. 15(b) is a view showing the distal portion side.

FIGS. 16(a) and 16(b) are perspective views illustrating an operational aspect of the tissue closing device shown in FIG. 1, in which FIG. 16(a) is overall view, and FIG. 16(b) is a view showing the distal portion side.

FIGS. 17(a) and 17(b) are perspective views illustrating an operational aspect of the tissue closing device shown in FIG. 1, in which FIG. 17(a) is an overall view, and FIG. 17(b) is a view showing the distal portion side.

FIGS. 18(a) and 18(b) are perspective views illustrating an operational aspect of the tissue closing device shown in FIG. 1, in which FIG. 18(a) is an overall view, and FIG. 18(b) is view showing the distal portion side.

Figure 19:
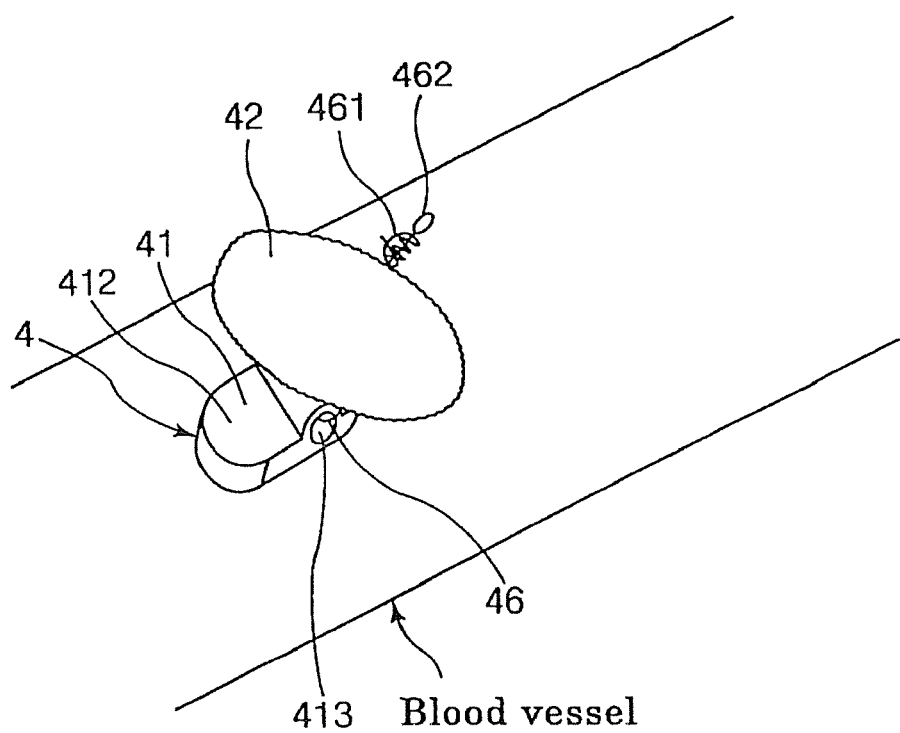

FIG. 19 is a perspective view illustrating an operational aspect of the tissue closing device shown in FIG. 1.

FIGS. 20(a)-(e) are cross-sectional views taken along the section line b-b of FIG. 1 illustrating an operational aspect of the tissue closing device shown in FIG. 1.

DETAILED DESCRIPTION

FIG. 1 illustrates, in perspective exploded view, features associated with an embodiment of the tissue closing device disclosed herein. The part surrounded by the broken line and the inside thereof are generally shown in FIG. 1 in an enlarged form. For purposes of convenience in description, the direction of arrow A in the figure is referred to as the "distal end", the direction of arrow B (hand-operated side) is referred to as the "proximal end", the direction of arrow C is referred to as the "upper side", and the direction of arrow D is referred to as the "lower side".

The tissue closing device 1 is a device for closing a transcutaneously penetrating puncture hole (opening which penetrates a living body tissue membrane) which is formed, for example, in a living body lumen such as a blood vessel, an internal organ of a living organism or a living body tissue membrane such as an internal tissue of a living organism.

As shown in FIGS. 1, 2, 5 and 6, the tissue closing device 1 includes an elongate arrangement device (delivery and deformation means) 3 having a distal portion configured to pass through a puncture hole (i.e., opening) penetrating tissue membrane, and having a hand-operated portion 9 on the proximal end and a clip 4 serving as a closure (i.e., tissue closure) which is detachably retained (mounted) at a distal portion of the arrangement device 3 to close the puncture hole penetrating the in tissue membrane.

Figure 2:
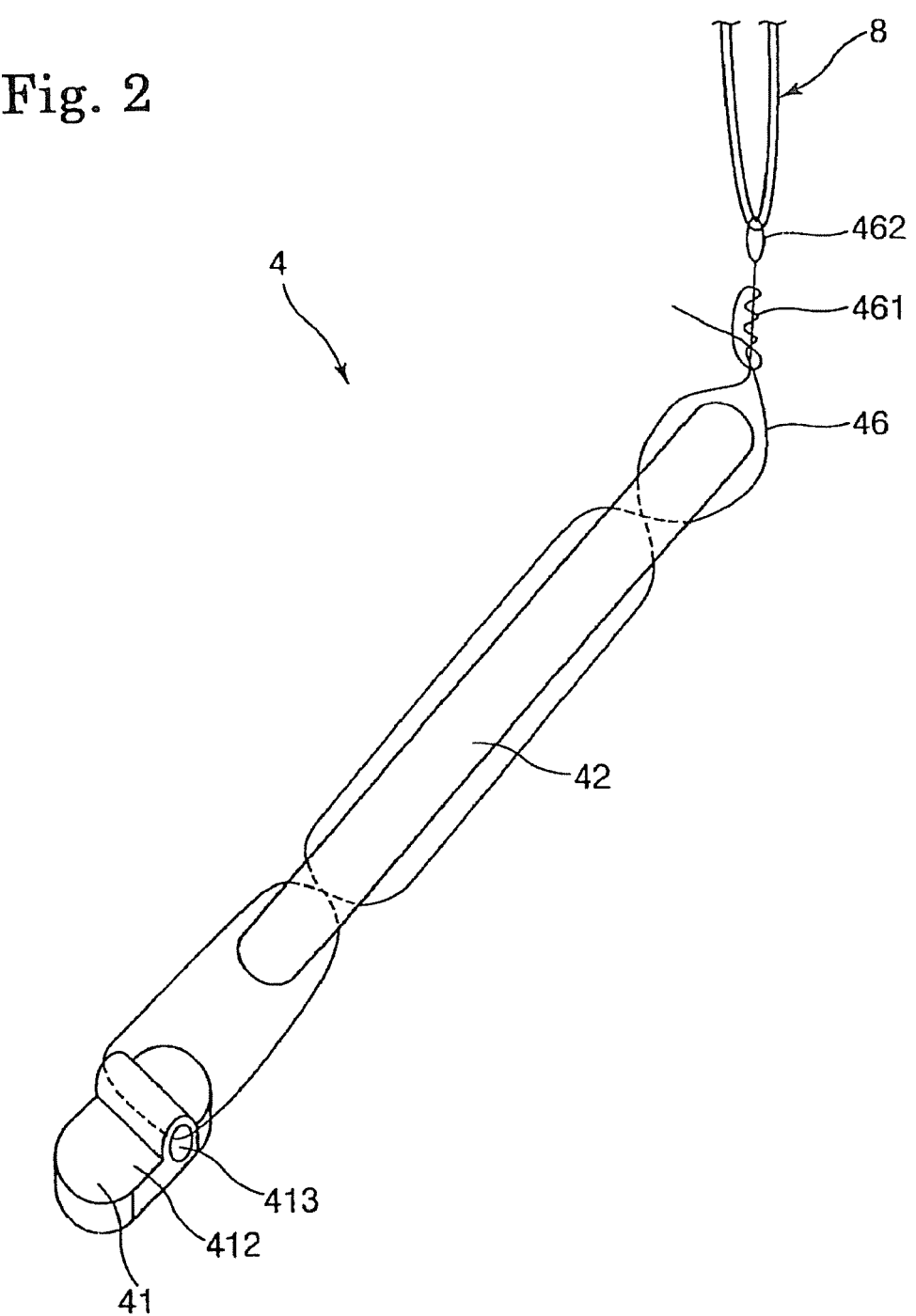
FIG. 2 is a perspective view of a closure used in the tissue closing device shown in FIG. 1.

As best illustrated in FIG. 2, the clip 4 includes a seal portion (anchor) 41, a deformation portion 42 which is deformable, and a first thread or thread-shaped element (inclusive of thread-like element) 46 functioning both as a connecting portion that connects the seal portion 41 and the deformation portion 42 to each other and as a fixing portion. In addition, the thread 46 has a knot 461 and a loop 462. Additional features associated with the clip 4 will be described in more detail below.

Figure 12:
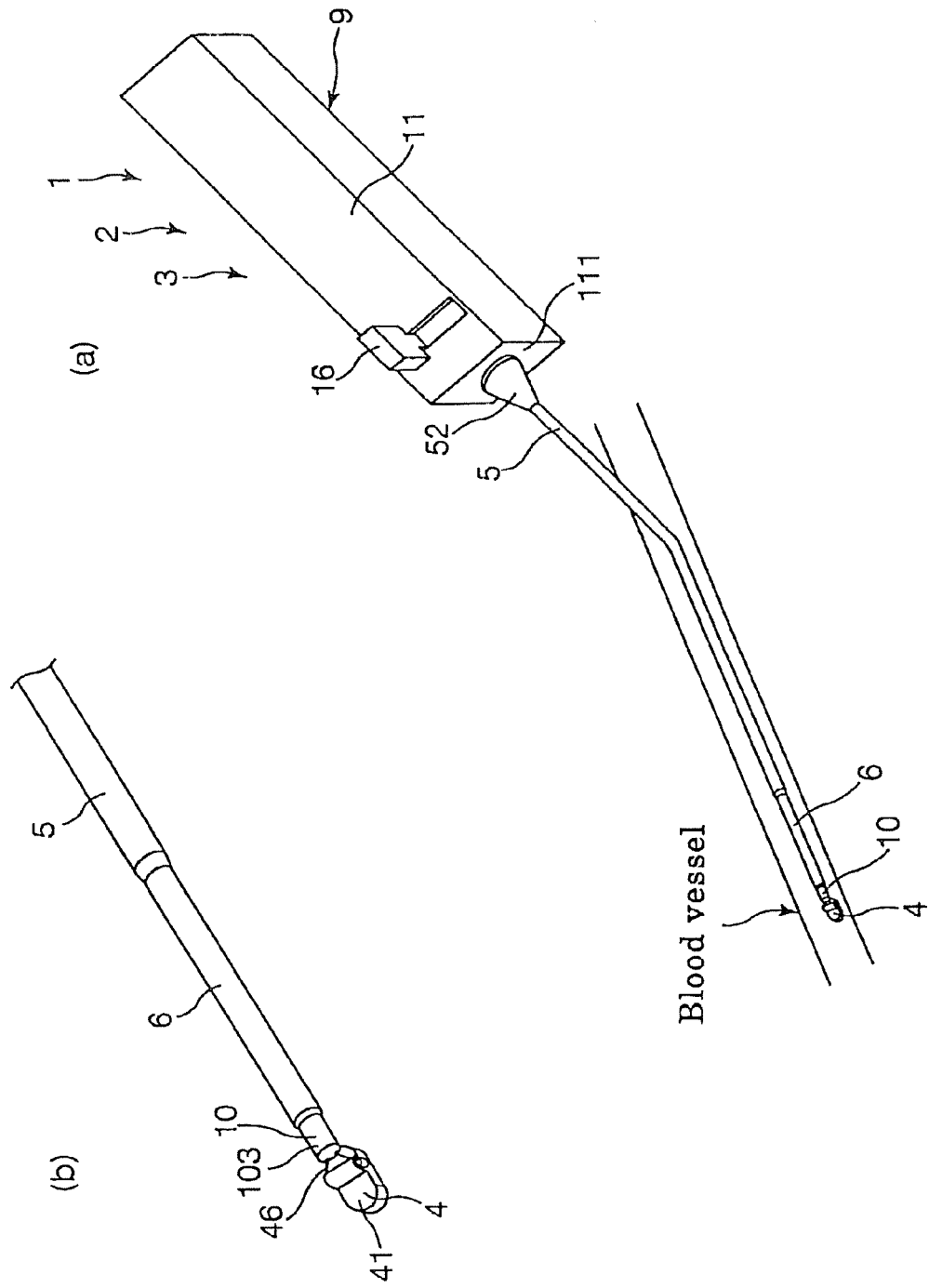

The arrangement device 3 is configured to be detachably or removably inserted in a sheath (i.e., elongate tubular body) 5 having a distal portion configured to pass through a puncture hole and a lumen 51 extending in the axial direction of the sheath. The arrangement device 3 is used in a condition in which the sheath 5 is detachably mounted to the arrangement device 3 as shown in FIG. 12. The sheath 5 and the arrangement device 3 constitute an elongate body portion 2. During a staunching operation (i.e., an operation for closing a puncture hole), distal portions of the sheath 5, the arrangement device 3 and the clip 4 penetrate the puncture hole, i.e., they are inserted through the puncture hole into a body lumen such as a blood vessel.

The sheath 5 has a substantially hollow cylindrical shape, and has a hub 52 at its proximal portion. In addition, a staunching valve (not shown) is disposed on the inner side of the hub 52.

The sheath 5 may be, for example, a sheath (introducer sheath) left indwelling after a therapeutic treatment (PCI) or diagnosis (CAG) using a catheter. Alternatively, the sheath 5 may be a sheath used exclusively in connection with the tissue closing device 1.

Incidentally, while the sheath 5 was mentioned above as being a component of the main body portion 2, it is to be understood that the sheath 5 may be considered as not being included in the components of the main body portion 2.

As shown in FIGS. 1, 2, 5 and 6, the arrangement device 3 comprises: a second thread or thread-shaped element (inclusive of thread-like element) 8 serving as a retaining member (retaining means) which is detachably connected to the clip 4 (i.e., connected to the thread 46 of the clip 4) and is operative to retain the clip 4 (i.e., retain the thread 46 of the clip 4); a cover tube (cover member or cover means) 6 serving as an elongated first tubular member (tubular body) with a distal portion configured to penetrate a puncture hole; a fixing tube (latching member or latching means) 7 serving as an elongated second tubular member (tubular body) with a distal portion capable of penetrating a puncture hole; a slit tube (storing member or storing means) 10 having an elongated third tubular member (tubular body) 101 and having a distal portion configured to penetrate a puncture hole; and a hand-operated portion 9.

The clip 4 is retained by the arrangement device 3 at a distal portion of the arrangement device 3 in such a manner that the thread 46 is detachably retained by the thread 8, the deformation portion 42 is stored in a storing portion 102 of the slit tube 10, and the seal portion 41 is located on the distal side relative to a support portion or liquid blocking portion 103 of the slit tube 10.

In addition, the slit tube 10 is concentrically disposed and positioned in the lumen of the cover tube 6, with the cover tube 6 being configured to be moved (slidably moved) relative to the slit tube 10 in the longitudinal direction. The fixing tube 7 is concentrically disposed and positioned in the lumen of the slit tube 10, and the fixing tube 7 is configured to be moved (slidably moved) relative to the slit tube 10 in the longitudinal direction. In addition, the thread 8 is disposed in the lumen of the fixing tube 7, and is configured to be moved relative to the fixing tube 7 in the longitudinal direction of the fixing tube 7. The hand-operated portion 9 is provided on the proximal side of the fixing tube 7, the slit tube 10 and the cover tube 6.

The proximal portion of the cover tube 6 is fixed to or supported by the distal portion of a casing 11 of the hand-operated portion 9.

In addition, the fixing tube 7 is formed from a comparatively hard material, and is fixed to or supported by the distal portion of a fixing tube support portion (latching member support portion) 12 of the hand-operated portion 9 as generally shown in, for example, FIGS. 5(a) and 5(b).

The slit tube 10 is fixed to or supported by a slit tube support portion (storing member support portion) 14 of the hand-operated portion 9 as also generally shown in, for example, FIGS. 5(a) and 5(b).

As illustrated in FIGS. 8-11, the slit tube 10 is comprised of a long tubular body or member 101, having a storing portion 102 for storing the deformation portion 42 of the clip 4 and a support portion (liquid block portion or spacer) 103 located on the distal side of the storing portion 102, supporting the thread 46 by clamping it at the boundary between the deformation portion 42 and the seal portion 41, and inhibiting or restraining a liquid influx, such as blood, into the storing portion 102. The deformation portion 42, such as a collagen plug, is thus protected from coming in contact with liquid such as blood.

In this case, the support portion 103 is provided at the distal portion of the tubular body 101, and the distal portion of the tubular body 101 is hermetically sealed. In other words, the distal portion of the slit tube 10 constitutes the support portion 103.

The part of the distal portion of the tubular body 101 on the proximal side relative to the support portion 103 constitutes the storing portion 102. The deformation portion 42 of the clip 4 is stored in the storing portion 102, namely in the lumen of the storing portion, on the proximal side relative to the support portion 103 of the distal portion of the tubular body 101.

The support portion 103 of the slit tube 10 is provided with a slit 104 for dividing the support portion 103 into a plurality of portions (two portions in this illustrated embodiment) to provide a deformation portion take-out port (opening-closing means) which can be opened and closed. The slit 104 extends along the longitudinal direction of the slit tube 10 over a range from the distal end (distal end face) of the support portion 103 to an intermediate portion of the storing portion 102. When the slit 104 is closed, penetration of a liquid into the storing portion 102 is inhibited or restrained. On the other hand, opening of the slit 104 permits the deformation portion 42 to be discharged exteriorly (taken out or removed) from the storing portion 102.

The support portion 103 of the slit tube 10 supports the thread 46 so that the seal portion 41 is pivotally turned (swung) relative to the slit tube 10 in a single plane around a predetermined one (the x-axis in FIG. 8) of three mutually orthogonal axes (the x-axis, y-axis, and z-axis in FIG. 8).

More specifically, the support portion 103 of the slit tube 10 is provided with a pair of holes 105 through which the thread 46 of the clip 4 (a pair of parts of the thread-like element) are passed.

Each of the holes 105 is formed along the longitudinal direction of the slit tube 10, parallel to the longitudinal axis of the slit tube 10, is open at the distal end face of the support portion 103 on one end side thereof, is open at the proximal end face of the support portion 103, and communicates with the storing portion 102.

In addition, the holes 105 are located at spaced apart positions from one another and at positions spaced apart (eccentrically) on opposite sides of the central axis (i.e., longitudinal axis) of the support portion 103. The two holes 105 are also located on the slit 104 so that a plane containing the slit 104 also passes through the holes 105.

The diameter of the holes 105 are sufficiently small so that with the thread 46 of the clip 4 inserted in each of the holes 105, the holes 105 do not substantially influence the function of the support portion 103 for inhibiting or restraining penetration of a liquid into the storing portion 102.

The thread 46 (a pair of parts of the thread-shaped element) of the clip 4 passes through the pair of holes 105, and the seal portion 41 is disposed on the distal side relative to the support portion 103 as generally illustrated in FIG. 11. The support of the thread at two points spaced apart from each other helps ensure that the seal portion 41 is turned relative to the slit tube 10 only around a predetermined one of the three mutually orthogonal axes. More specifically, the passage of the thread 46 through the holes 105 helps ensure that turning of the seal portion 41 around the y-axis and the z-axis in FIG. 8 is inhibited or restrained, so that the seal portion 41 is turned substantially only around the x-axis. In other words, the seal portion 41 is pivotally turned along a straight line formed by intersection of the slit 104 with the distal face of the support portion 103 (the straight line in a radial direction of the distal face) as an axis of turning. The pair of holes 105 is positioned on the straight line which is vertical to the longitudinal direction of the blood vessel so that the portion 41 is turned in the single plane containing the axis of the blood vessel.

The seal portion 41 has an elliptical shape or chamfered rectangular shape, and is provided near its central portion with a hole 413 formed along a direction orthogonal to the longitudinal direction of the seal portion 41. The hole 413 is for passing the thread 46 therethrough so that the seal portion 41 is supported at two points. Therefore, the seal portion 41 is supported in such a manner that the four points including the two spaced points set by the hole 413 and the two spaced points set by the holes 105, 105 are connected by the thread 46, resulting in the seal portion 41 being turned substantially only around the x-axis. Here, the x-axis is an axis orthogonal to the axis of the blood vessel, and it is therefore ensured that the seal portion 41 is turned only in a single plane containing the axis of the blood vessel. Accordingly, the longitudinal direction of the seal portion 41 can be made to coincide with the axis of a blood vessel, irrespective of the magnitude of the angle at which the puncture hole formed between the skin and the blood vessel is inclined relative to the blood vessel.

The slit tube 10 may be formed, for example, as a single piece, or may be formed by joining a plurality of pieces (i.e., separate members) to each other (e.g., by adhesion with an adhesive, fusing, or other means).

The positional relationships between the cover tube 6, the fixing tube 7 and the slit tube 10 in the longitudinal direction of the arrangement device 3 are set so that the distal end of the slit tube 10 is located distal-most, the distal end of the cover tube 6 is located intermediately, and the distal end of the fixing tube 7 is located on proximal-most.

In this embodiment, the distal end of the cover tube 6 is located on the sidewall of the support portion 103 of the slit tube 10. In other words, the cover tube 6 covers the outer surface of the slit tube 10, exclusive of the distal portion of the support portion 103 (i.e., a part on the distal side of the slit tube 10). Thus, the inner surface of the cover tube 6 faces the outer surface of the slit tube 10, exclusive of the distal portion of the support portion 103.

In addition, the distal end of the fixing tube 7 is located on the proximal side relative to the slit 104 of the slit tube 10 (i.e., on the proximal side of the deformation portion 42 of the clip 4) and the knot 461 of the thread 46 is located between the proximal end of the deformation portion 42 and the distal end of the fixing tube 7 as illustrated in FIG. 11.

When the thread 46 of the clip 4 is pulled in the proximal direction by the thread 8, the knot 461 of the thread 46 is latched by a distal portion 71 of the fixing tube 7. Further, the deformation portion 42 is latched through the knot 461 (i.e., indirectly latched), whereby the knot 461 is moved relative to the distal direction and the thread 46 is thereby tightened, resulting in the deformation portion 42 being deformed and locked.

The elongated portion of the arrangement device 3 is configured to be inserted into the lumen 51 of the sheath 5 from the proximal side of the sheath 5 until a connector 111 of the arrangement device 3 is connected to the hub 52 of the sheath 5. At this time, the distal portions of the cover tube 6 and the slit tube 10 protrude from the distal end of the sheath 5 and the distal portion of the cover tube 6 is exposed from the distal end of the sheath 5 as shown in FIG. 11. Therefore, the distal end of the sheath 5 is located on the proximal side relative to the distal ends of the cover tube 6 and the slit tube 10.

Figure 5:
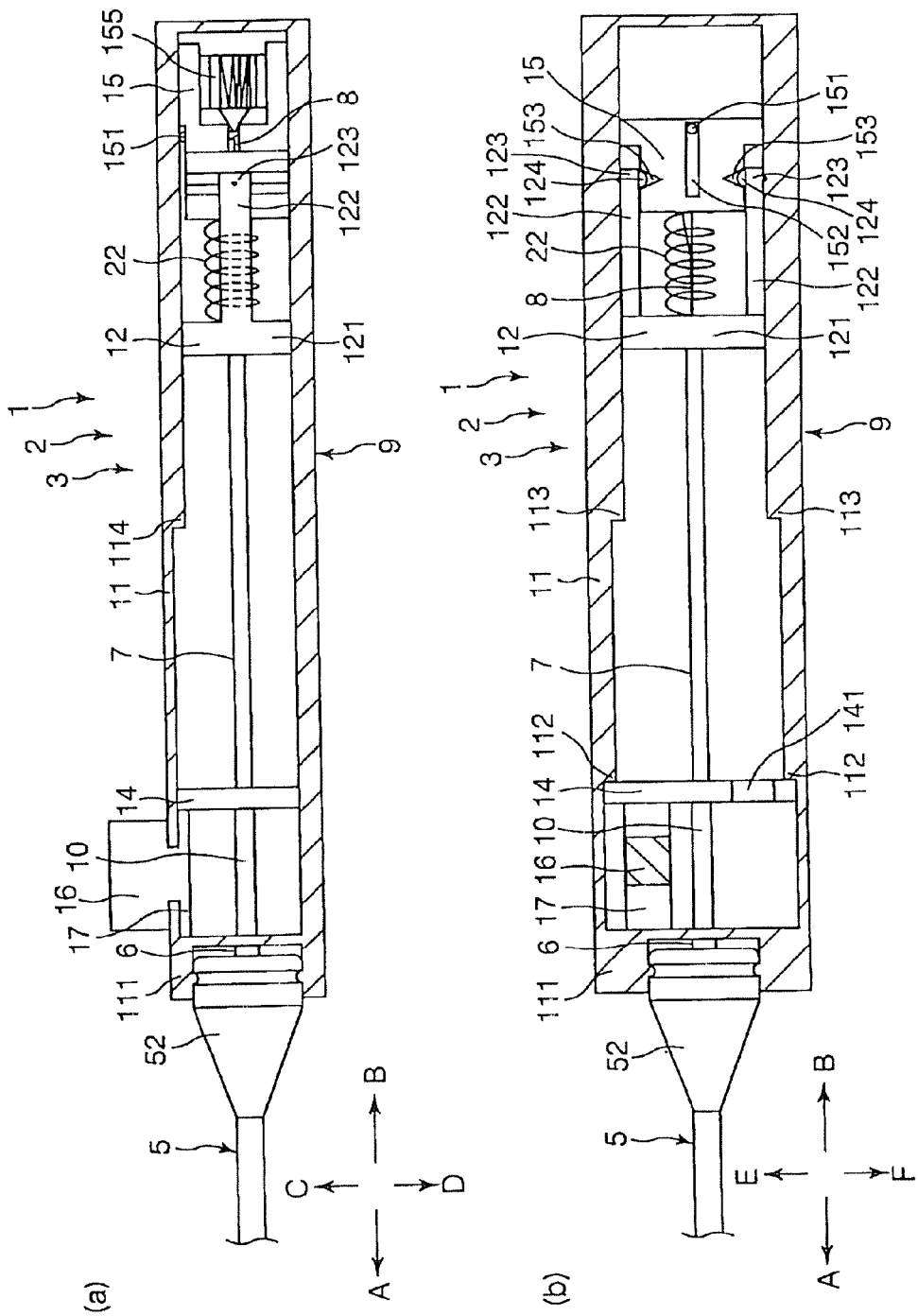
Figure 6:
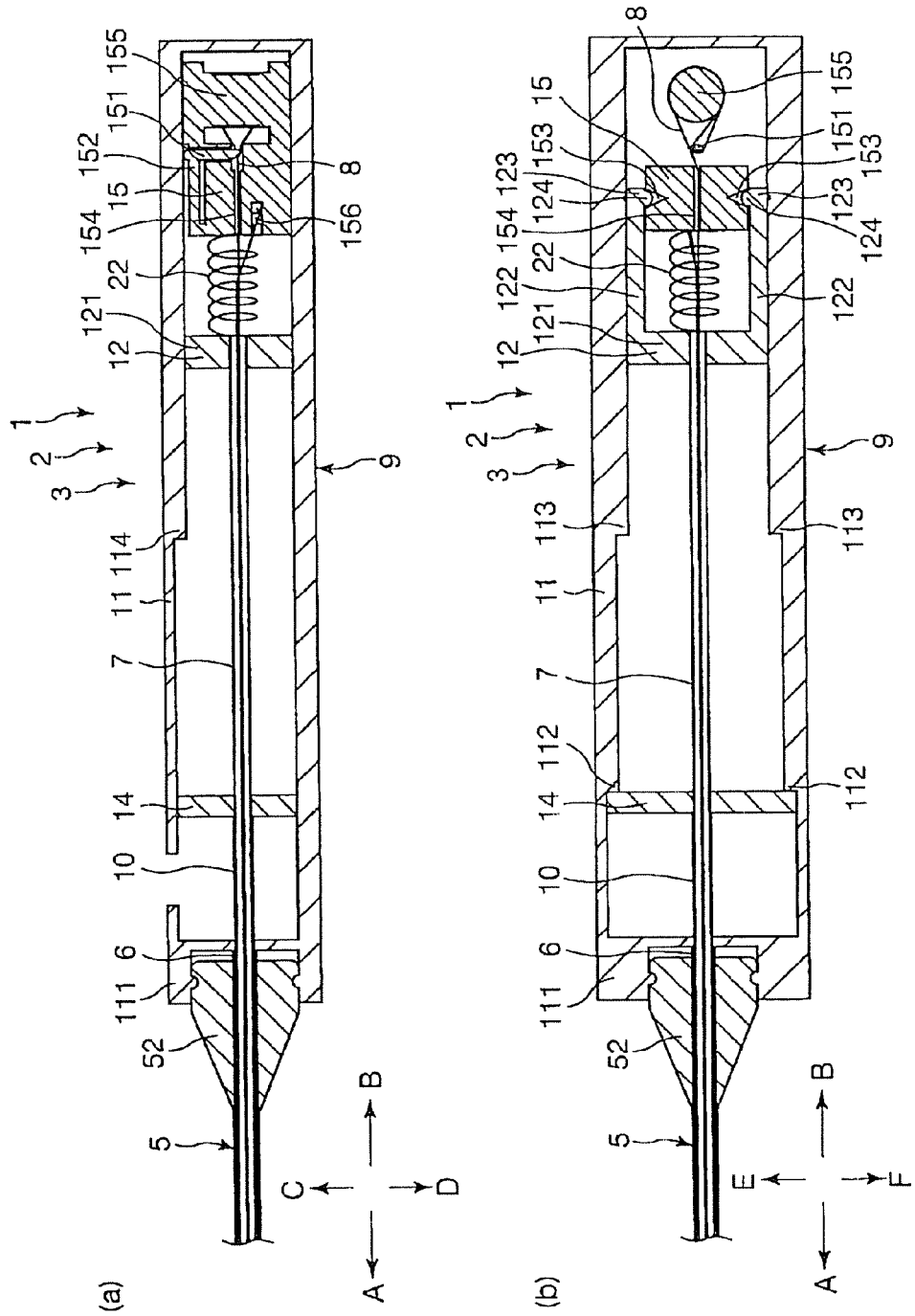

As shown in FIGS. 1, 5 and 6, the hand-operated portion 9 comprises a casing (main body) 11, a fixing tube support portion (latching member support portion) 12 for supporting the fixing tube 7, a slit tube support portion (storing member support portion) 14 for supporting the slit tube 10, a thread support portion (retaining member support portion) 15 for supporting the thread 8, a coil spring 22 which is an elastic member (actuating member), a lever (knob) 16, and a lock portion 17 joined to the lower side of the lever 16.

The casing 11 has a tubular shape (polygonal tubular shape) which is substantially rectangular parallelepiped.

The distal portion of the casing 11 is provided with the connector 111 configured to be fitted to the hub 52 of the sheath 5. The inner surface of the connector 111 has an annular rib (flange) configured to engage a groove on the outer surface of the hub 52. When the hub 52 is inserted into the connector 111 (i.e., when the connector 111 is fitted to the hub 52), the rib of the connector 111 is engaged with the groove of the hub 52 so that the sheath 5 is connected to the casing 11 (the arrangement device 3).

The cover tube 6 is fixed at a central portion of the inside of the connector 111, and the connector 111 is provided in the central portion with a hole through which the slit tube 10 passes.

In addition, the interior of the casing 11 is provided with a pair of stepped portions (engaging portions) 112, a pair of stepped portions (engaging portions) 113, and a stepped portion (engaging portion) 114.

The pair of stepped portions 112 are formed at both side portions of a distal portion of the casing 11, the pair of stepped portions 113 are formed at both side portions of a central or intermediate portion of the casing 11, and the stepped portion 114 is formed at an upper portion of the central or intermediate portion of the casing 11.

The slit tube support portion 14, the fixing tube support portion 12 and the thread support portion 15 are disposed in the interior of the casing 11 so that they are movable in the longitudinal direction of the arrangement device 3.

The slit tube support portion 14 is tetragonal plate-like in shape, and both side portions thereof are latched by the stepped portions 112, whereby it is inhibited from moving in the proximal direction.

In addition, the slit tube support portion 14 is provided, at its end portion in the direction of arrow F in FIG. 5(*b*), with a cutout portion 141 open in both the distal direction and the proximal direction.

The slit tube 10 is fixed to a central portion of the slit tube support portion 14, and the slit tube support portion 14 is provided in its central portion with a hole through which the fixing tube 7 passes.

The lever 16 is an operating part or operating member for changeover between a condition where the slit tube support portion 14, the fixing tube support portion 12, the thread support portion 15 and the coil spring 22 are inhibited from moving relative to the casing 11 (i.e., a locked condition) and a condition in which the relative movements are permitted (i.e., an unlocked condition). The lever 16 is disposed on the upper side, and exterior, of the casing 11 so as to be movable (slidable) in the directions of the arrows E or F in FIG. 5(*b*).

The lock portion 17 having a plate-like shape is joined to the lower side of the lever 16 so that the lever 16 and the lock portion 17 are moved together as a single unit. The lock portion 17 is located on the upper side in the interior of the casing 11, and between the connector 111 and the slit tube support portion 14.

When the lever 16 is located in the locking position as shown in FIGS. 1 and 5, the lock portion 16 contacts an upper portion of the connector 111 at one end side and an upper portion of the slit tube support portion 14 at the other end side thereof, so that the slit tube support portion 14 is locked by the lock portion 16. The slit tube support portion 14 is thus inhibited from moving in the distal direction. In other words, the slit tube support portion 14, the fixing tube support portion 12, the thread support portion 15 and the coil spring 22 are inhibited from moving in the distal direction. Thus, actuation of the coil spring 22 is restricted.

In addition, when the lever 16 is moved in the direction of arrow F until the endmost position (i.e., an unlocking position), the lock portion 17 is moved into alignment with the position of the cutout portion 141 of the slit tube support portion 14. In this position, the locking of the slit tube support portion 14 by the lock portion 16 is canceled and so the slit tube support portion 14 can be moved in the distal direction. In other words, the slit tube support portion 14, the fixing tube support portion 12, the thread support portion 15 and the coil spring 22 are permitted to move in the distal direction, whereby the actuation of the coil spring 22 is permitted.

The device thus includes a changeover means for effecting a changeover between a locked condition where the action of triggering the coil spring (actuating member) 22 by the trigger means is forbidden and an unlocked condition where such action is permitted. In the illustrated embodiment, the lever 16 and the lock portion 17 constitute the changeover means.

The fixing tube support portion 12 is composed of a base portion 121 and a pair of guides 122, formed as rod-shaped bodies, projecting in the proximal direction from both side portions of the base portion 121.

The fixing tube 7 is fixed to a central portion of the base portion 121 of the fixing tube support portion 12. The base portion 121 of the fixing tube support portion 12 is provided at its central portion with a hole through which the thread 8 passes.

The guides 122 are provided at their proximal portions 123 with projections 124 which project inwards towards one another so that the projections face each other. The fixing tube support portion 12 is located near the proximal portion of the casing 11 and on the distal side of the thread support portion 15.

Figure 7:
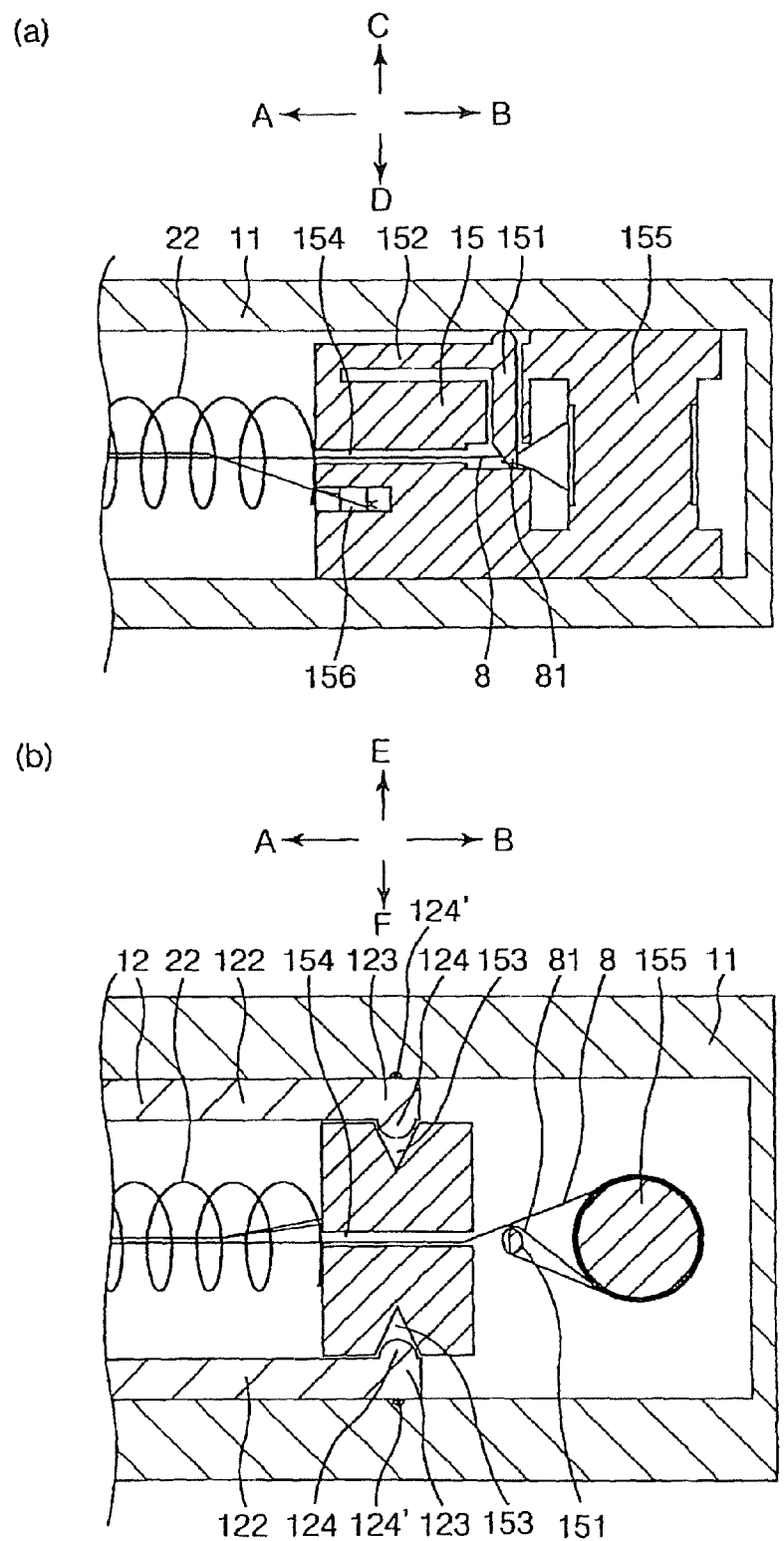

The thread support portion 15 is located at the proximal portion of the casing 11 and on the proximal side of the fixing tube support portion 12. As shown in FIG. 7, the distal portion of the thread support portion 15 with a pair of notches 153 into which the projections 124 of the pair of guides 122 of the fixing tube support portion 12 are engaged (inserted). More specifically, the projections 124 of the fixing tube support portion 12 are engaged with the notches 153 of the thread support portion 15, whereby the fixing tube support portion 12 and the thread support portion 15 are detachably connected. This ensures that the thread support portion 15 and the fixing tube support portion 12 are moved together.

In addition, as shown in FIG. 7(b), minute projections 124' are provided at the proximal portions of the guides 122 at positions aligned with the projections 124 and on the outer surfaces of the guides 122. Each of the minute projections 124' is fitted in a respective recessed portion formed in the casing 11, and functions as a safety device for preventing the guides 122 (indirectly, the clip 4) from moving (sliding) relative to the casing 11 unless a load not less than a predetermined value (i.e., a reference value) is exerted on the guides 122. The predetermined value or reference value refers to a value such that the user can confirm a secure contact of the seal portion 41 of the clip 4 with a blood vessel. Preferably, a value of about 450 to 550 gf is adopted as the reference value. This helps prevent the clip 4 from dropping into the blood vessel.

The thread support portion 15 is provided with a pin (i.e., connecting means) 151 for detachably connecting the thread 8 to the thread support portion 15. The pin 151 is movable in the vertical direction through the rod 152 (turnable about a tip portion of the rod 152). In the illustrated embodiment, the pin 151 is integrally formed in one piece with the rod 152. The lower end portion of the pin 151 is provided on its distal side with an inclined surface such that the width of the pin 151 is gradually decreased along the downward direction. The lower end of the pin 151 abuts on the thread support portion 15 so that no gap is formed between the lower end portion of the pin 151 and the thread support portion 15. An upper end portion of the pin 151 abuts on the inside surface of the casing 11 so that the pin 151 is inhibited from moving upward. A turned-back portion 81 of the thread 8 is hooked on the pin 151, and this configuration helps prevent the turned-back portion 81 of the thread 8 from coming off (being released from) the pin 151.

The thread support portion 15 is provided in its distal portion with a passage 154 through which the thread 8 passes. The thread support portion 15 is provided at its proximal portion with a bobbin 155 around which the thread 8 is wound.

The thread 8 is composed of a double thread (double thread-shaped element) which has a single thread (thread-shaped element) turned back on itself, with the an end portion on one side being the turned-back portion 81. In addition, the thread 8 is attached to the thread support portion 15 by tying both end portions of the thread in a singular state so that it is hooked on the clasp 156 formed at the distal portion of the thread support portion 15.

The thread 8 is passed through the clip 4 (the loop 462 of the thread 46 of the clip 4), is turned back at a distal portion of the arrangement device 3 and retains the clip 4. Moreover, the thread 8 is passed through the passage 154 of the thread support portion 15 and wound around the bobbin 155 a number of times, and further the turned-back portion 81 thereof is hooked on the pin 151 so that the turned-back portion 81 is detachably connected to the thread support portion 15 by the pin 151. As has been mentioned above, an end portion on the other side (the opposite end portion of the turned-back portion 81) is attached to the clasp 156 of the thread support portion 15.

As shown in FIGS. 5 and 6, the coil spring 22 is disposed between the base portion 121 of the fixing tube support portion 12 and the thread support portion 15. The coil spring 22 is disposed in a contracted state (active state), with its distal end abutting on the proximal face of the base portion 121 of the fixing tube support portion 12 and its proximal end abutting on the distal face of the thread support portion 15.

As shown in FIG. 2, the clip (i.e., closure) 4 includes the seal portion 41, the deformation portion 42 which is deformable, and the thread (first thread-shaped element) 46 serving both as a fixing portion and a connecting portion for connecting the seal portion 41 and the deformation portion 42 to each other. That is, the seal portion 41 and the deformation portion 42 are connected to each other through the thread 46.

The seal portion 41 is plate-shaped and possesses a flat plate portion (flat surface) 412 to be brought into close contact with a puncture hole and its surrounding tissue membrane from one side (inner side) of the tissue membrane so as to cover the puncture hole and the surrounding tissue.

The seal portion 41 is provided in its central portion with the hole (through-hole) 413 in which the thread 46 is inserted (passed). The hole 413 extends along a direction substantially perpendicular to the thickness direction of the seal portion 41 and a narrow side direction of the seal portion 41. That is, the hole 413 is open at both side surfaces of the seal portion 41.

The surface on the upper side and the surface on the lower side, as viewed in FIG. 2, of the seal portion 41 are each a flat surface (inclusive of substantially flat), not including the region or portion where the hole 413 is formed.

The deformation portion 42 has a substantially cylindrical shape, generally elongated in form, in an initial state prior to deformation as shown in FIG. 2. The distal portion and proximal portion of the deformation portion 42 are rounded in shape.

The deformation portion 42 is constituted of a porous material. The deformation portion 42 can be deformed from the initial state shown in FIG. 2 into a state in which the deformation portion 42 on the other side (outer side) of the tissue membrane cooperates with the seal portion 41 to sandwich a puncture hole therebetween, thereby closing the puncture hole. Examples of porous materials which can be used to fabricate the deformation portion 42 include deformable assemblies of fibers, such as fibrous mass, woven fabric, nonwoven fabric and elastic materials such as foam (i.e., spongy materials). In addition, preferable examples of the material constituting the deformation portion 42 include staunching materials such as collagen, cellulose oxide and bio-absorbable materials.

Examples of preferred materials constituting the seal portion 41 and the thread 46 include bio-absorbable materials. This ensures that the clip 4 is absorbed into the living body after a predetermined period, and is not eventually left in vivo, so that its influence on the human body can be negated or avoided. Examples of the bio-absorbable materials include polylactic acid, polyglycolic acid, and polydioxanone, which may be used either singly or in combination.

In the case where the tissue membrane is a blood vessel wall (body lumen wall), the surface on one side (inner side) is the surface farther from the body surface of the blood vessel wall (body lumen wall), i.e., the inner surface of the blood vessel wall (body lumen wall), and the surface on the other side (outer side) is the surface nearer to the body surface of the blood vessel wall (body lumen wall), i.e., the outer surface of the blood vessel wall (body lumen wall).

Figure 3:
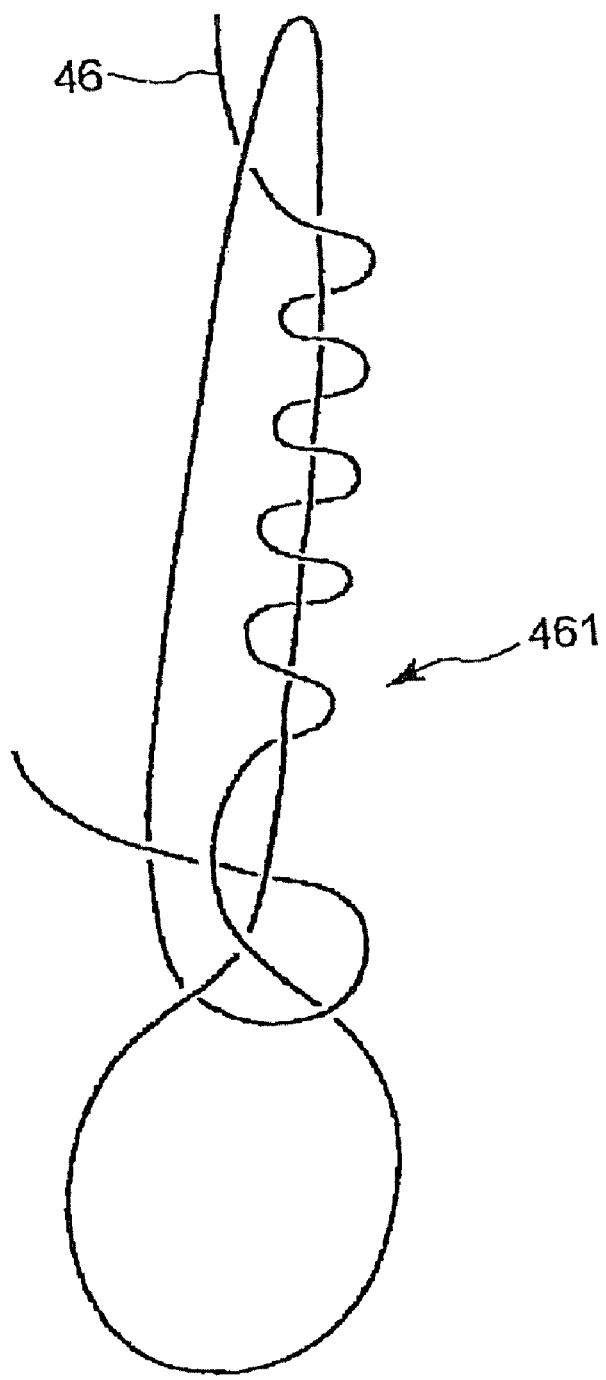
FIG. 3 is an illustration of one example of a knot used with the closure shown in FIG. 2.
Figure 4:
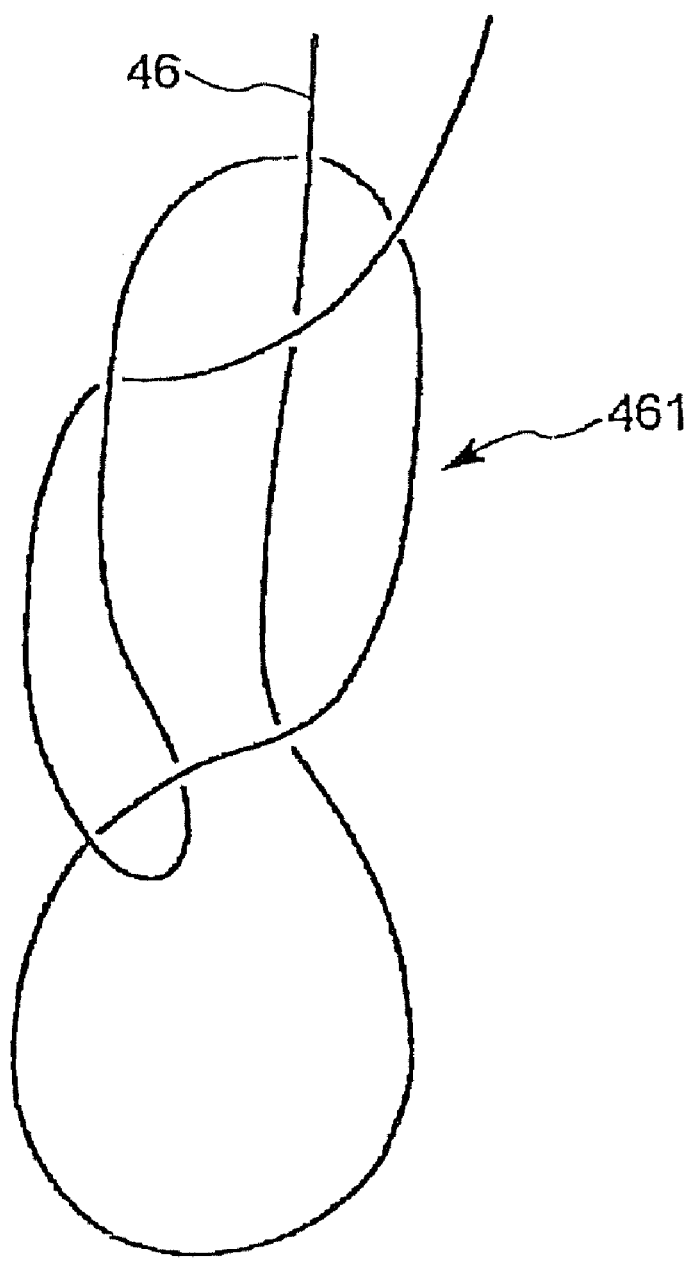
FIG. 4 is an illustration of another example of a knot used with the closure.

In the condition where the thread 46 is passed through the hole 413 in the seal portion 41 and is turned back to thereby retain the seal portion 41, both end portions of the thread 46 are passed crosswise through two portions of the deformation portion 42 (a distal portion and a proximal portion of the deformation portion 42) and are made to form the knot 461 shaped as shown in FIG. 3 or 4, on the proximal side relative to the proximal end of the deformation portion 42. Such a knot is called a clinch knot. In addition, the loop 462 through which to pass the thread 8 is formed on the upper side of the knot 461 in FIG. 2.

The portion on the distal side of the thread 46, i.e., a substantially loop-shaped portion inclusive of a pair of parts of the thread (thread-shaped element) on the distal side, is used to connect the seal portion 41 and the deformation portion 42 to each other. Thus, the distal-side portion of the thread 46 functions as a connecting portion for connecting the seal portion 41 and the deformation portion 42 to each other. The thread 46 extends to the proximal side of the deformation portion 42, and the extended portion of the thread 46 constitutes a fixing portion for the deformation portion 42.

The knot 461 is so formed as to be movable in the distal direction (i.e., downward in FIG. 2). With the thread 46 tightened by moving the knot 461 toward the distal end of the thread 46, the deformation portion 42 is deformed from the initial form into a predetermined form, and the resulting condition can be retained. When the thread 46 is retaining the condition where the deformation portion 42 has been deformed into the predetermined form, the knot 461 of the thread 46 is located at an end portion (proximal portion), on the opposite side of the seal portion 41 from the deformation portion 42. Since the knot 461 is in the state of strongly fastening the thread 46, the knot 461 is not likely to be spontaneously moved in the proximal direction unless a sufficiently strong force is exerted thereon.

The knot 461 is formed to be larger than the inside diameter (lumen diameter) of the fixing tube 7, while the loop 462 is formed to be smaller than the inside diameter (lumen diameter) of the fixing tube 7. This helps ensure that the fixing tube 7 can move the knot 461 so as to fasten the thread 46 and deform the deformation portion 42 because the loop 462 can be inserted into the lumen of the fixing tube 7, and the knot 461 can be prevented from entering into the lumen of the fixing tube 7. In this manner, the thread 46 functions as a fixing portion for the deformation portion 42.

As has been mentioned above, the thread 8 passes through the lumen of the fixing tube 7 in the state of being passed through the loop 462 of the thread 46. The thread 46 may serve also as the thread 8. In that case, after the deformation portion 42 is deformed and fixed by the thread 46, the thread 46 may be cut by scissors on the proximal side of the knot 461.

In addition, the thread 46 may be composed of a double thread (double thread-shaped element) which has a single thread (thread-shaped element) turned back and which has an end portion on one side constituting the turned-back portion, and the loop 462 may be composed of the turned-back portion.

Operational aspects of the clip 4 according to one disclosed embodiment are now discussed. When the thread 46 of the clip 4 is pulled in the proximal direction by the thread 8, the knot 461 of the thread 46 is latched at the distal portion 71 of the fixing tube 7, and the deformation portion 42 is latched (relatively pushed) through the knot 461, whereby the knot 461 is moved in the distal direction. The thread 46 is thus tightened, and the deformation portion 42 is compressed and deformed.

In other words, as the knot 461 is moved in the distal direction and the thread 46 is tightened, the deformation portion 42 is gradually collapsed from the initial form and continuously deformed into a form in which the seal portion 41 and the deformation portion 42 can cooperate with each other in sandwiching a tissue membrane therebetween, thereby closing a puncture hole.

As mentioned above, the knot 461 is so formed as to be movable in the distal direction only when so strong a force is exerted thereon, so that the condition where the deformation portion 42 is deformed into the predetermined form is retained by the thread 46.

Thus, according to the clip 4 as above, the degree of deformation (i.e., the manner of collapse) of the deformation portion 42 can be continuously controlled (adjusted). Specifically, the deformation portion 42 can be deformed into any desired form. This makes it possible to cope with various situations such as people (patients) with thicker membrane, thinner membrane, harder membrane, softer membrane, etc. with respect to a tissue membrane such as blood vessel wall. The deformation portion 42 is thus able to cope with, and be used in connection with, various conditions (situations) of tissue membrane.

Set forth below is a description of operational aspects of a staunching operation which can be performed using the tissue closing device 1. The operation of the tissue closing device 1 will be described below.

As shown in FIG. 12, after a therapeutic treatment (PCI) or diagnosis (CAG) using a catheter, a sheath 5 can be left indwelling, and this sheath 5 will be used. The distal portion of the sheath 5 penetrates the puncture hole and is positioned in the blood vessel.

In an initial condition, the lever 16 is located in the locking position, and the lock portion 17 abuts on the distal side of the slit tube support portion 14. The slit tube support portion 14 is thus inhibited from moving in the distal direction.

First, as shown in FIG. 12 and FIG. 20(a), the operator (user) gradually inserts the arrangement device 3 into the lumen 51 of the sheath 5 from the proximal side of the sheath 5, and connects the connector 111 to the hub 52 of the sheath 5. As a result, the rib of the connector 111 is fitted in the groove of the hub 52, and the sheath 5 is mounted to the arrangement device 3 (casing 11). Then, a distal portion of the cover tube 6 and the support portion 103 of the slit tube 10 protrude from a distal portion of the sheath 5, and the seal portion 41 of the clip 4 also protrudes to be inserted into the blood vessel.

In this condition, the slit 104 of the slit tube 10 is in its closed state so that blood is inhibited from flowing into the storing portion 102 of the slit tube 10, and the deformation portion 42 of the clip 4 is prevented from being swollen through contact with the blood in the blood vessel. Therefore, relatively high safety is secured.

Next, as shown in FIG. 13, the casing 11 of the hand-operated portion 9 is gripped with fingers and the hand-operated portion 9, i.e. the main body portion 2 (arrangement device 3), is slowly moved in a direction for drawing out of the puncture hole (in the proximal direction), to cover the puncture hole and the surrounding tissue of the puncture hole with the seal portion 41 of the clip 4 from the inner side of the blood wall vessel (to position and anchor the seal portion 41). The deformation portion 42 of the clip 4 is thus moved to the outside of the blood vessel.

During the time the puncture hole and the peripheral portion surrounding the puncture hole are covered with the seal portion 41, the operator moves the main body part 2 in the direction of drawing out from the puncture hole and, when he or she senses a resistance (surface contact resistance) upon contact of the seal portion 41 with the puncture hole and the peripheral tissue surrounding the puncture hole, he or she judges that the seal portion 41 has come into contact (surface contact) with the puncture hole and the peripheral tissue surrounding the puncture hole. The positioning of the seal portion 41 is thus deemed completed.

In this case, the members for connecting the clip 4, the thread support portion 15, and the casing 11 along the longitudinal direction of the arrangement device 3 do not include a member expandable in the longitudinal direction of the arrangement device 3, such as a spring, and the distance between the clip 4 and the casing 11 is maintained at a substantially constant value. Therefore, the operator can sense directly with his or her fingers the force exerted on the seal portion 41 of the clip 4, whereby it is possible to accurately sense the resistance upon contact of the seal portion 41 of the clip 4 with the puncture hole and the peripheral tissue surrounding the puncture hole.

In addition, since the turnings of the seal portion 41 of the clip 4 around the y-axis and the z-axis in FIG. 8 are each inhibited or restrained and the seal portion 41 substantially is turned only around the x axis, the posture of the seal portion 41 can be regulated easily and accurately.

Further, since the slit tube support portion 14, the fixing tube support portion 12, the thread support portion 15 and the coil spring 22 are inhibited by the lock portion 17 from moving in the distal direction, the coil spring 22 can be securely prevented from being triggered before the positioning of the seal portion 41 is completed.

Due to these features, the seal portion 41 of the clip 4 can be positioned relatively easily and assuredly.

Next, as shown in FIG. 14, the lever 16 is moved in the direction of the arrow F, to be shifted to the unlocking position. As a result, the lock portion 17 is moved in the direction of the arrow F, i.e., moved (retracted) into the position in alignment with the cutout portion 141 of the slit tube support portion 14, whereby the locking of the slit tube support portion 14 by the lock portion 16 is canceled. This enables the slit tube support portion 14, the fixing tube support portion 12, the thread support portion 15 and the coil spring 22 to be moved in the distal direction.

Subsequently, the main body portion 2 (arrangement device 3) is slowly moved in the direction of drawing out from the puncture hole (in the proximal direction), thereby drawing out the main body portion 2 from the puncture hole. By this operation, all the operations (motions) are conducted sequentially and continuously, the puncture hole is closed with the clip 4, and the clip 4 is kept disposed (indwelling) in the living body. Now, the procedure and operation in this regard will be described in more detail below.

Figure 15:
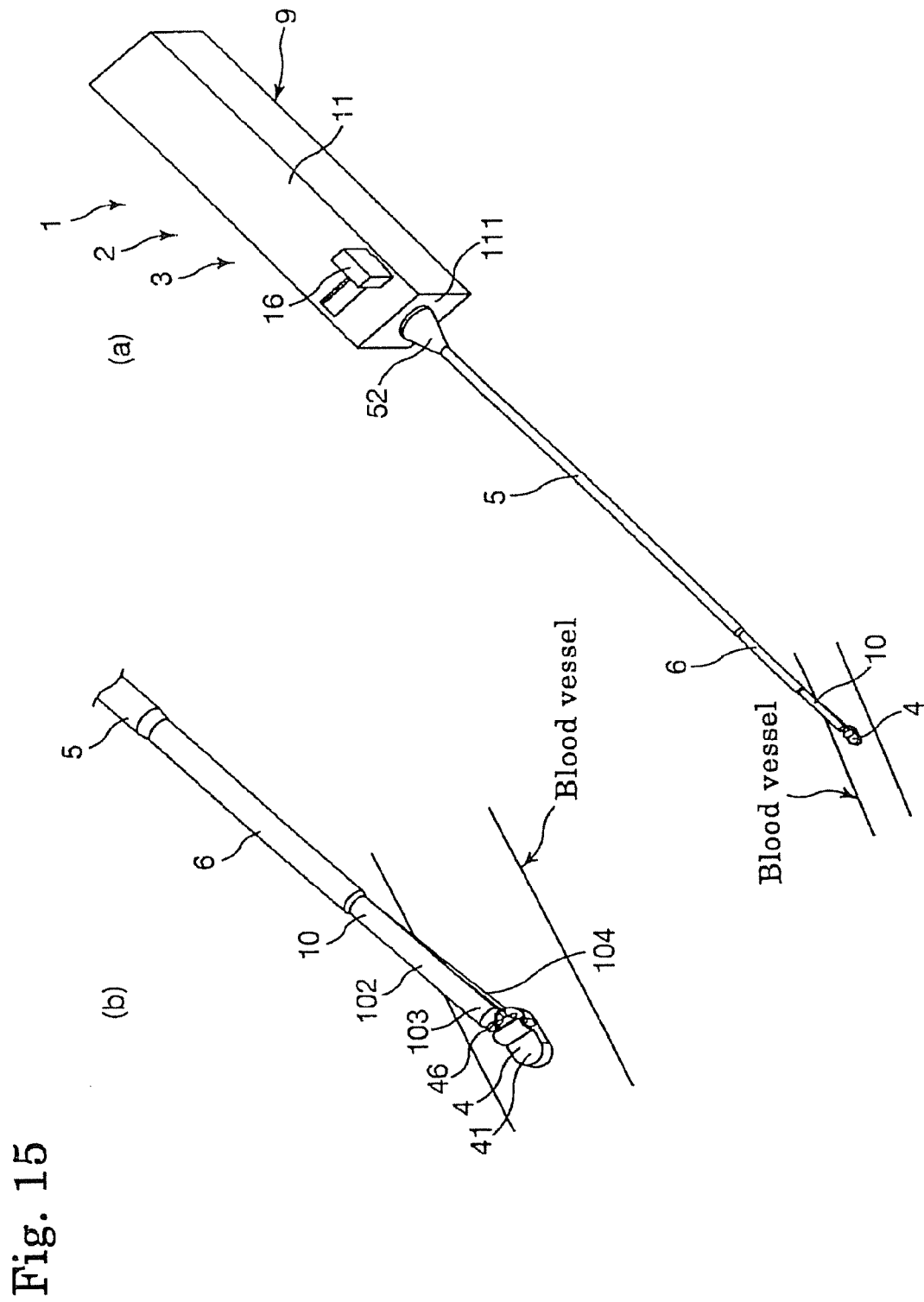

First, as shown in FIG. 15 and through a comparison of FIG. 20(a) and FIG. 20(b), when the hand-operated portion 9 (casing 11) is moved in the proximal direction, the thread support portion 15, the fixing tube support portion 12, the coil spring 22 and the slit tube support portion 14 are inhibited from moving in the proximal direction because the seal portion 41 of the clip 4 is in contact with the inner surface (the surface farther from the body surface) of the blood vessel wall, and the casing 11, the cover tube 6 and the sheath 5 are moved in the proximal direction. Specifically, the cover tube 6 is moved in the proximal direction relative to the slit tube 10, whereby the portion of the slit tube 10 ranging from the support portion 103 to an intermediate portion of the storing portion 102 of the slit tube 10 protrudes (is exposed) from or beyond the distal portion of the cover tube 6, and the slit tube 10 is split at the slit 104 (or the condition where the slit 104 can be opened is established).

Figure 16:
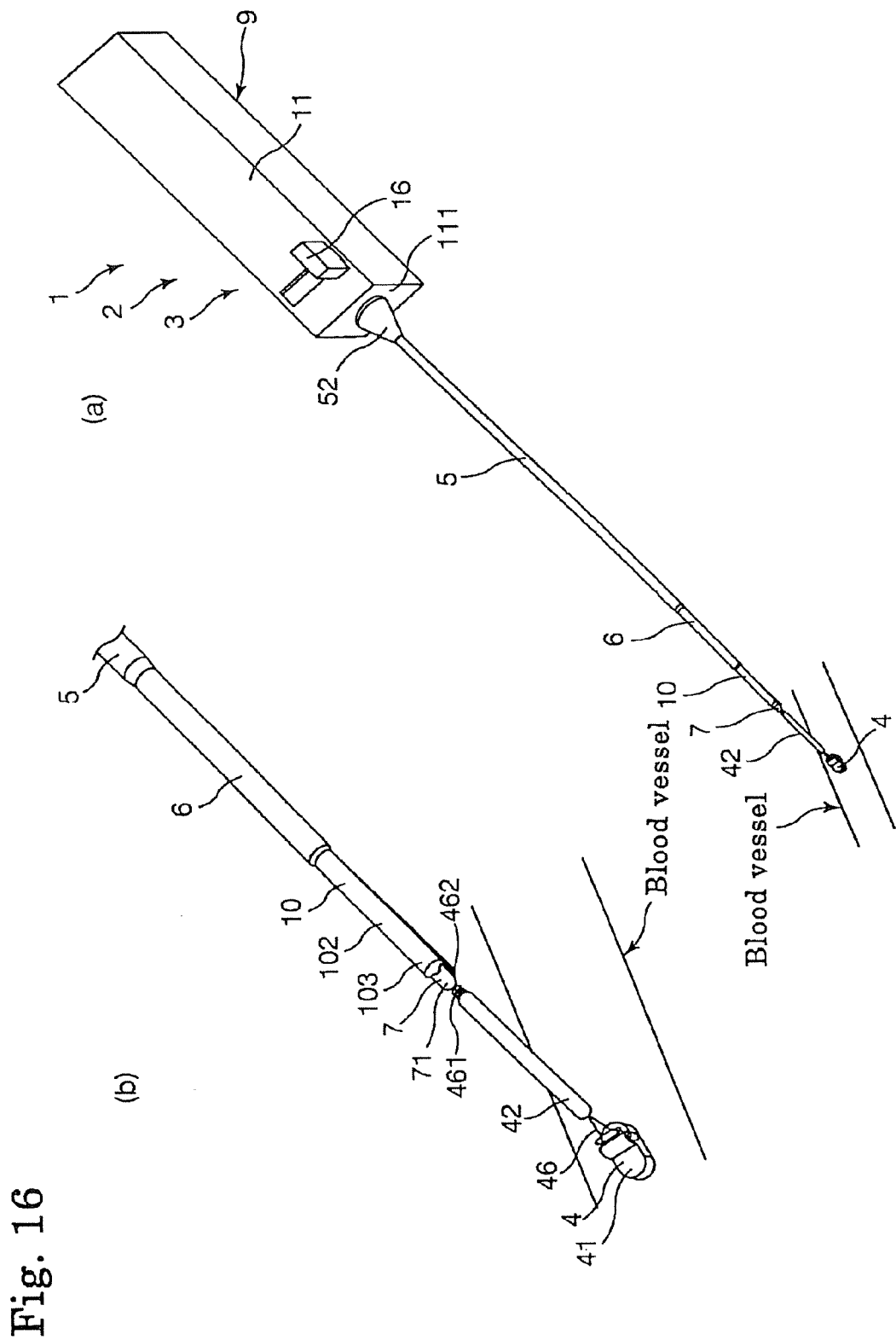

As shown in FIG. 16 and FIG. 20(c), when the hand-operated portion 9 (casing 11) is further moved in the proximal direction, the slit tube support portion 14 comes into contact with the distal portion of the inner surface of the casing 11 and is thereby inhibited from moving in the distal direction relative to the casing 11, so that thereafter the slit tube support portion 14 is moved in the proximal direction together with the casing 11. More specifically, the slit tube 10 is moved in the proximal direction relative to the fixing tube 7, whereby the deformation portion 42 of the clip 4 is pushed in the distal direction by the fixing tube 7 and is discharged from the storing portion 102 to the exterior. At this time, since the slit 104 is opened, the deformation portion 42 can be easily discharged from the storing portion 102.

Figure 17:
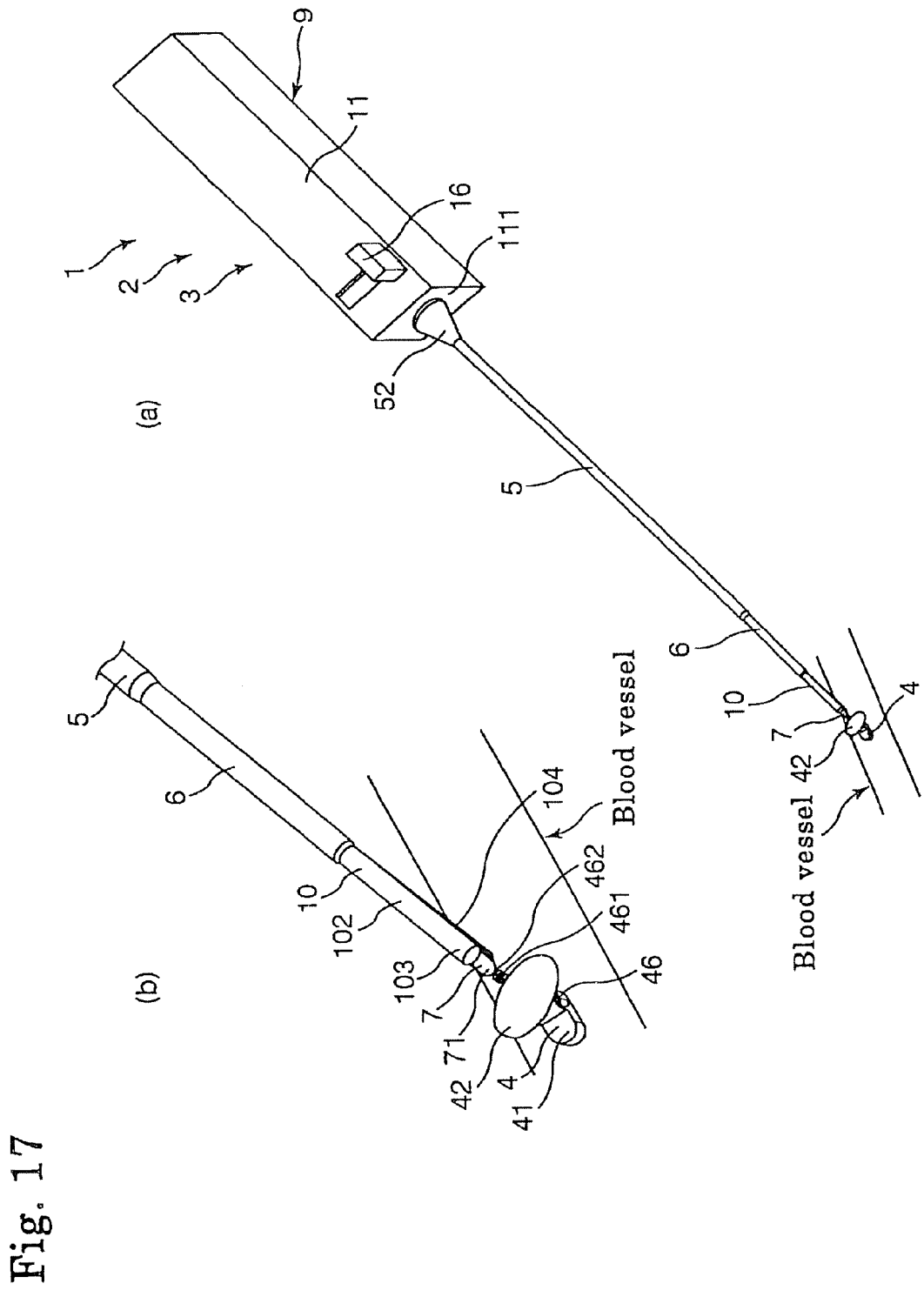

As shown in FIG. 17 and FIG. 20(d), when the hand-operated portion 9 (casing 11) is further moved in the proximal direction, the fixing tube support portion 12, the thread support portion 15 and the coil spring 22 are moved in the distal direction relative to the casing 11, and so the proximal portions 123 of the guides 122 of the fixing tube support portion 12 are moved to the distal side relative to the stepped portions 113, i.e., the inner cavity of larger width. As a result, a condition is established in which the proximal portions 123 of the guides 122 can be moved (displaced) respectively to lateral sides (in the directions of arrows E and F). On the other hand, the fixing tube support portion 12 is energized in the distal direction relative to the thread support portion 15 by the restoring force of the coil spring 22, and the energizing force moves the proximal portions 123 of the guides 122 substantially sideways along the inside surfaces of the notches 153, whereby the projections 124 of the guides 122 are disengaged from the notches 153 of the thread support portion 15.

As a result of this, the connection between the fixing tube support portion 12 and the thread support portion 15 is canceled to establish a condition in which the thread support portion 15 can be moved in the proximal direction relative to the fixing tube 7. The cancellation of the connection between the fixing tube support portion 12 and the thread support portion 15 makes possible relative movement of the thread support portion 15 and the fixing tube support portion 12, thus canceling the restriction that retains the coil spring 22 in a compressed state (active state). The coil spring 22 is thus triggered.

As a result of this, the thread support portion 15 is moved in the proximal direction relative to the fixing tube support portion 12 and the fixing tube 7 by the restoring force of the coil spring 22. Thus, the pair of guides 122 of the fixing tube support portion 12, the pair of notches 153 of the thread support portion 15, and the region (space) on the distal side of the stepped portions 113 of the casing 11 function as trigger means for triggering the coil spring 22 by canceling the restriction that retains the coil spring 22 in the active state. In addition, the pair of guides 122 of the fixing tube support portion 12 and the pair of notches 153 of the thread support portion 15 function as restricting means for retaining the coil spring 22 in the active state. The motion (triggering motion) for moving the proximal portions 123 of the guide 122 of the fixing tube support portion 12 that connect the thread support portion 15 and the fixing tube support portion 12 to each other in a lateral direction (in the direction in which the projections 124 of the guides 122 are disengaged from the notches 153 of the thread support portion 15) is automatically carried out by the operator's motion of evulsing (moving) the hand-operated portion 9 to the proximal side and the energizing force of the coil spring 22.

As shown in FIG. 17 and FIG. 20(d), when the thread support portion 15 is moved in the proximal direction relative to the fixing tube 7, the thread 8 is moved in the proximal direction, the thread 46 of the clip 4 is pulled by the thread 8 in the proximal direction, the knot 461 of the thread 46 of the clip 4 is latched at the distal portion 71 of the fixing tube 7, and the deformation portion 42 is latched through the knot 461 (latched indirectly), whereby the knot 461 is moved in the distal direction, the thread 46 is tightened, and the deformation portion 42 is deformed.

As a result, the deformation portion 42 covers the puncture hole and the surrounding tissue of the puncture hole from the outside of the blood vessel wall, the seal portion 41 covers the puncture hole and its surroundings from the inside of the blood vessel wall, and the blood vessel wall is sandwiched between the seal portion 41 and the deformation portion 42, whereby the puncture hole is closed. The condition in which the deformation portion 42 is deformed in this manner is kept (fixed) by the thread 46.

Figure 18:
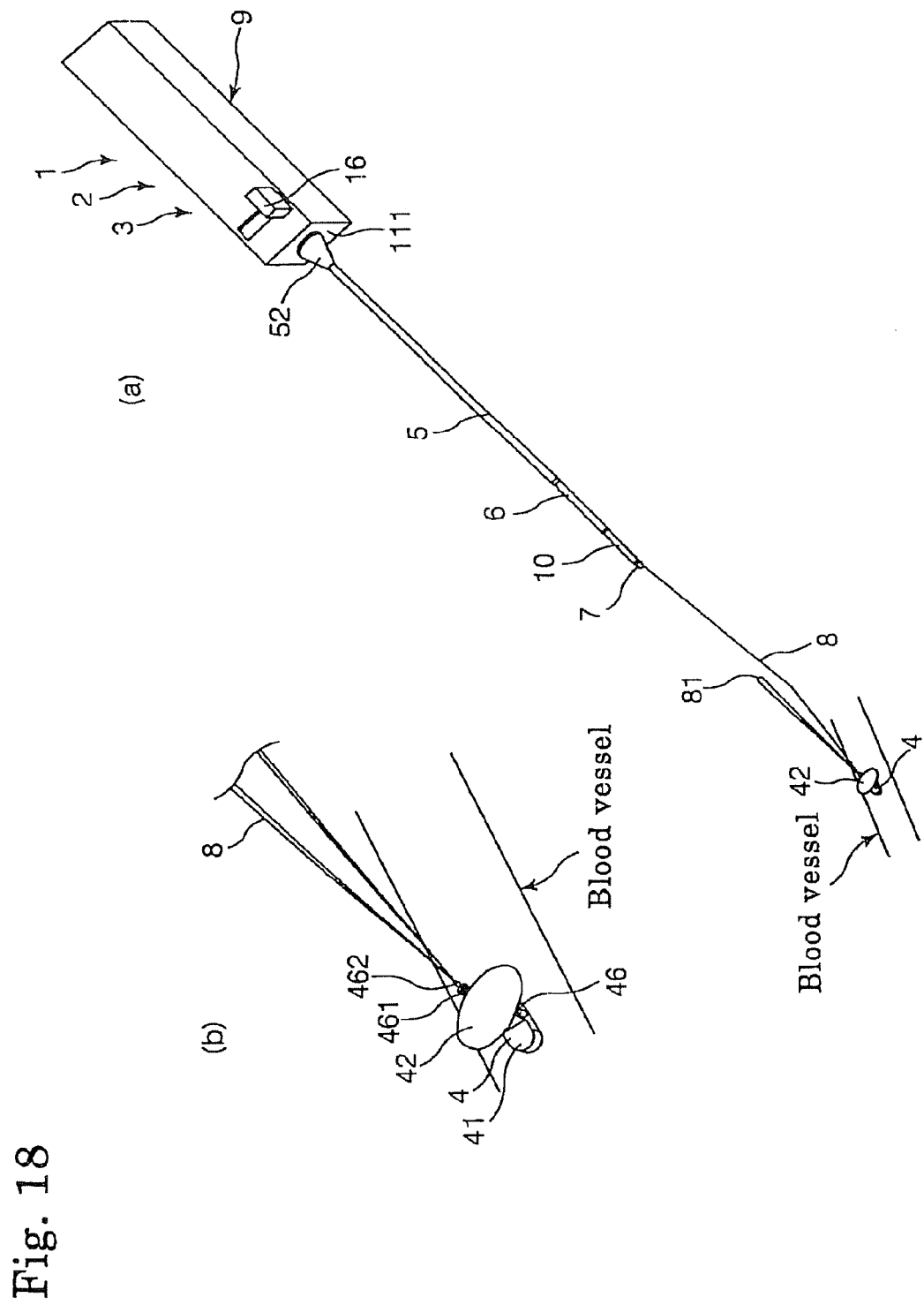

In addition, after the connection between the fixing tube support portion 12 and the thread support portion 15 (the restriction for retaining the coil spring 22 in the active state) is canceled, i.e., after the deformation of the deformation portion 42 of the clip 4 is completed, the hand-operated portion 9 (casing 11) is further moved in the proximal direction as shown in FIG. 18 and FIG. 20(e), whereupon the casing 11 is further moved in the proximal direction relative to the thread support portion 15. In other words, the thread support portion 15 is further moved in the distal direction relative to the casing 11.

Then, when the pin 151 of the thread support portion 15 is moved to the distal side relative to the stepped portions 114, the pin 151 is permitted to be moved (displaced) upwards (in the direction of arrow C). On the other hand, with the turned-back portion 81 of the thread 8 pulled in the proximal direction, the pin 151 is moved upwards by the action of the inclined surface thereof (see FIG. 6(a)), forming a gap between the lower end portion of the pin 151 and the thread support portion 15.

In this manner, the connection between the thread 8 and the thread support portion 15 by the pin 151 is canceled, whereby the connection between the thread 8 and the thread 46 of the clip 4 is canceled (the condition where the clip 4 is retained by the thread 8 is canceled). Specifically, the turned-back portion 81 of the thread 8 is disengaged from the pin 151, with the result being that the thread 8 is able to be drawn out from the loop 462 of the thread 46 of the clip 4. Therefore, the portion (space) on the distal side of the stepped portions 114 of the casing 11 constitutes connection canceling means (disconnecting means) and retained condition canceling means.

Then, when the hand-operated portion 9 (casing 11) is continuously moved in the proximal direction, only the main body portion 2 (ranging to the sheath 5, the cover tube 6, the slit tube 10 and the distal portion of the fixing tube 7) is firstly evulsed or removed/withdrawn from the patient. At this stage, as shown in FIG. 18, the turned-back portion 81 of the thread 8 is located exterior of the patient while being not drawn out of the loop 462 of the thread 46 of the clip 4 so that the clip 4 is retained by the thread 8.

More specifically, this tissue closing device 1 comprises the thread 8 which is wound around the bobbin 155 of the thread support portion 5 a number of times, and the length of the thread 8 is set to be comparatively large in the initial condition. Therefore, at the stage immediately after the evulsion of the main body portion 2 from the patient, the turned-back portion 81 of the thread 8 is not yet drawn out of the loop 462 of the thread 46 of the clip 4, so that the clip 4 is retained by the thread 8, and the turned-back portion 81 is located exterior of the patient. Therefore, the operator can keep retaining (securing) the clip 4 through the thread 8, by gripping the main body portion 2 and the turned-back portion 81 of the thread 8. This permits the operator to cope with various situations, whereby relatively high safety is secured. In this case, for example, the operator can take out the clip 4 present in the blood vessel by an operation while retaining the clip 4 through the thread 8.

Figure 20:
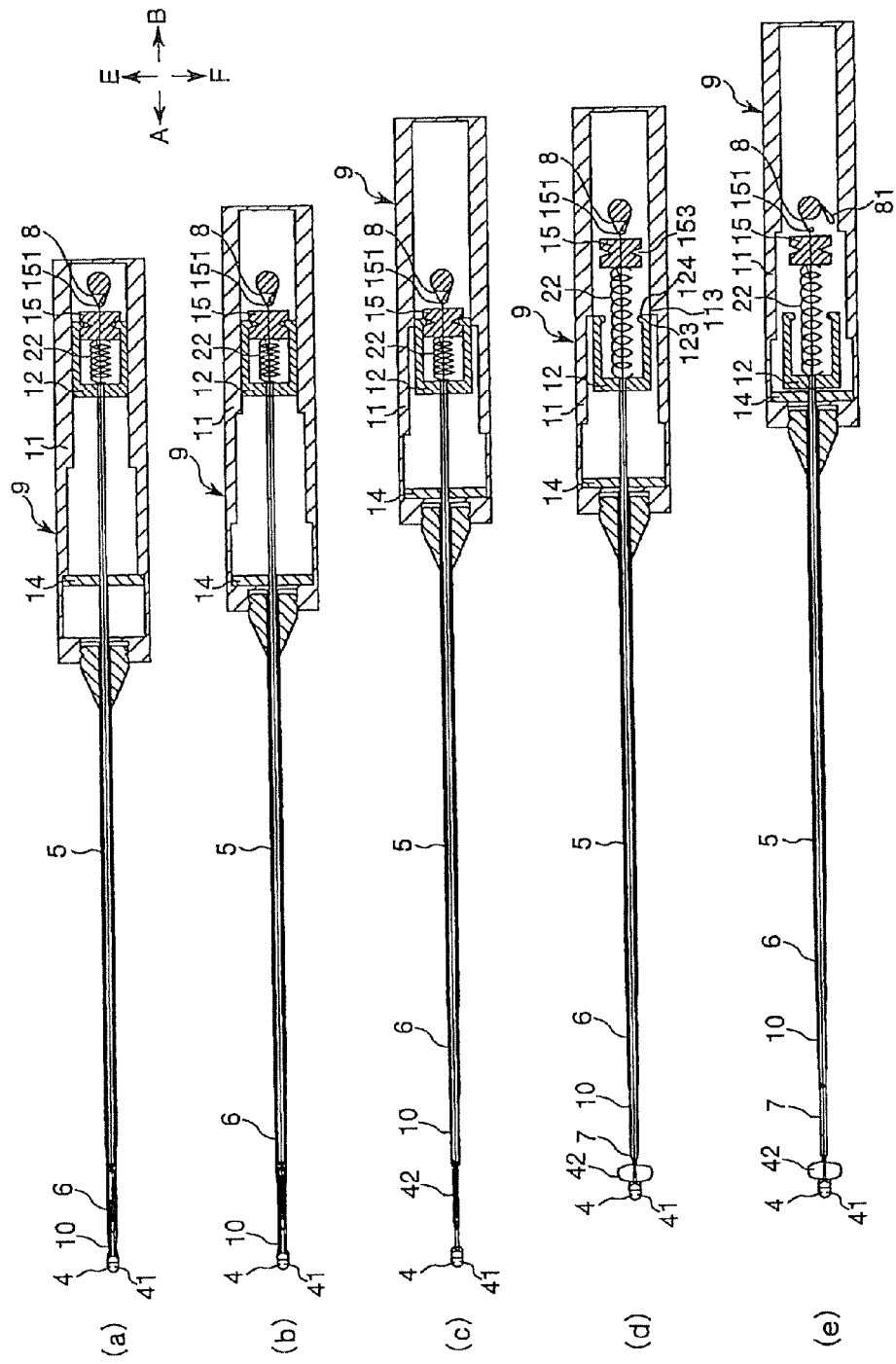

If there is no problem, the hand-operated potion 9 (casing 1) is further moved in the proximal direction as shown in FIG. 20, to evulse or remove the thread 8 from the patient. As a result, only the clip 4 is left disposed (indwelling) in the living body.

As has been described above, according to the tissue closing device 1 of the embodiment, the deformation portion 42 of the clip 4 is prevented from making contact with the blood in a blood vessel, and a relatively high safety is secured.

In addition, by only moving the hand-operated portion 9 (casing 11) in the proximal direction (single direction), all the operations (motions) are effected or carried out without need for any operator's (user's) operation, whereby the puncture hole is closed with the clip 4, and the clip 4 can be left disposed (indwelling) in the living body. Therefore, the operations can be relatively easily made even by a single hand, and a staunching operation for the puncture hole formed in a tissue membrane such as a blood vessel wall can be carried out relatively easily, speedily and assuredly. That is, a puncture hole can be closed relatively easily, speedily and assuredly, and satisfactory staunching can be achieved.

Particularly, since the deformation portion 42 of the clip 4 is deformed by the restoring force of the coil spring 22, it is unnecessary for the operator to deform the deformation portion 42 of the clip 4 through a manual operation, and a generally constant fastening force can always be obtained. Therefore, a puncture hole can be closed quite easily, speedily and assuredly.

Also, in the condition where the deformation portion 42 of the clip 4 has been deformed in a desired form, such condition can be maintained by the thread 46. This makes it possible to cope with various conditions (situations) of the tissue membrane.

While the tissue closing device here has been described based on the embodiment shown in the drawing figures and described above, the invention is not limited to the particular embodiment described and shown, and the configurations of the components can be replaced with any other configurations that have functions equivalent to the above. In addition, other features or components may be added to the device.

For example, the configuration of the clip (closure) is not limited to that in the above described embodiment insofar as the clip (closure) has a seal portion, a deformation portion and a connecting portion. For instance, the connecting portion and the fixing portion may be provided separately.

In addition, the canceling (trigger means) of the restriction for retaining the coil spring (elastic member) as the actuating member in the deformed state (active state) may be carried out, for example, by a switch or button operation.

In the above-described embodiment, the deformation portion is deformed by relative movements of the closure and the latching member in the condition where the closure is locked by the latching member which are effected through triggering the actuating member by the trigger means. However, the device is not limited in this respect. For example, the deformation of the deformation portion may be effected by those relative movements of the closure and the latching member which are made by an operator's manual operation.

In addition, while a configuration has been adopted in the above-described embodiment in which one of the two end portions of the thread 8 is fixed in the hand-operated portion 9 and the other is canceled from the connected state, a configuration wherein both end portions of the thread 8 are simultaneously canceled from the connected state may be adopted as an alternative. In that case, the thread 8 is left on the living body side in the state of being connected to the clip 4. Thereafter, the thread 8 can be freely evulsed or removed by an operator's procedure.

The features, principles and manner of operation of the tissue closure device according to a preferred embodiment has been described in the foregoing specification. However, the invention which is intended to be protected is not to be construed as limited to the particular embodiment and variations disclosed. Further, the embodiment described herein is to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A tissue closing device for closing an opening penetrating a tissue membrane in a living body, comprising:
    a closure configured to close the opening, the closure comprising a seal portion for covering the opening and tissue membrane surrounding the opening from one side of the tissue membrane, a deformation portion which is deformable, and a connecting portion connecting the seal portion and the deformation portion, the seal portion having a first longer axis and a second shorter axis and the seal portion being directly supported by the connecting portion at two points along the second shorter axis; and
    an arrangement device detachably retaining the closure for arranging the closure in the living body;
    the arrangement device comprising:
    a storing member having a longitudinal axis comprising a storing portion and a support portion, the storing member being configured for passage through the opening, the support portion comprising a take-out port which is divisible into a plurality of portions and configured to be opened from a closed state, the support portion being located on the distal side of the storing portion and supporting the connecting portion at a region between the deformation portion and the seal portion when the take-out port of the support portion is in a closed state, the closure being retained by the arrangement device so that the deformation portion is stored in the storing portion and the seal portion is located on the distal side relative to the support portion; and
    a hand-operated portion provided on the proximal side of the storing member;
    wherein the connecting portion passes through a passage of the seal portion and exits from the passage at two openings spaced apart from each other along the second shorter axis of the seal portion, and the connecting portion passes through the deformation portion;
    wherein the support portion possesses a pair of through holes which communicate the storing portion with the exterior of the storing member and a slit which communicates with the pair of through holes, the take-out port is opened by opening of the slit and closed by closing of the slit such that the connecting portion is retained within the pair of through holes and prevented from movement outside of the through holes along an axis transverse to the longitudinal axis of the storing member when the take-out port is in the closed state, and
    wherein the pair of through holes support the connecting portion so that the seal portion is pivotally turnable in a single plane around a predetermined one of three mutually orthogonal axes relative to the storing portion when the take-out port is in the closed state, with the deformation portion being discharged exterior of the storing member by opening of the take-out port.

2. The tissue closing device according to claim 1, wherein the storing member is a tubular body in which is defined the storing portion, the support portion being positioned at a distal portion of the tubular body, and the storing portion in which is stored the deformation portion being positioned on a proximal side of the tubular body relative to the support portion.

3. The tissue closing device according to claim 1, wherein the support portion is configured to restrain a liquid influx into the storing portion when the take-out port is in the closed state.

4. The tissue closing device according to claim 1, wherein the take-out port comprises said slit.

5. The tissue closing device according to claim 1, wherein:
    the connecting portion comprises two parts of a thread-shaped element; and
    the seal portion is pivotally turned around the predetermined one of the three mutually orthogonal axes relative to the storing member by passing each of the two thread-shaped elements through one of the through holes.

6. The tissue closing device according to claim 5, wherein the take-out port comprises said slit.

7. The tissue closing device according to claim 6, wherein the pair of holes are located at positions offset from a central axis of the support portion on opposite sides of the central axis, the pair of holes being positioned so that a plane containing the slit also passes through the pair of holes.

8. The tissue closing device according to claim 1, wherein the closure comprises a fixing portion which retains the deformation portion in a deformed condition.

9. The tissue closing device according to claim 8, wherein the fixing portion is comprised of a thread-shaped element possessing a movable knot.

10. The tissue closing device according to claim 8, wherein the connecting portion comprises of a thread-shaped element, the thread-shaped element comprising an extended portion extending to the proximal side of the deformation portion, and the fixing portion composed of the extended portion of the thread-shaped element.

11. The tissue closing device according to claim 1, wherein:
    the arrangement device comprises a cover member covering an outside surface of the storing member; and
    the cover member being movable in the proximal direction relative to the storing member to cause the support portion of the storing member to extend distally beyond the distal end of the cover member to establish a condition in which the take-out port is openable from the closed state.

12. The tissue closing device according to claim 1, wherein when the storing member is moved in the proximal direction in a condition in which the seal portion is in contact with a surface of the tissue membrane spaced from a body surface of the tissue membrane and the take-out port is openable from the closed state, the deformation portion is discharged from the storing portion to the exterior.

13. The tissue closing device according to claim 1, wherein:
the arrangement device comprises a latching member configured to pass through the opening penetrating the tissue membrane and latching at least a part of the closure; and
the deformation portion is deformed by relative movements of the closure and the latching member when the closure is latched to the latching member.

14. The tissue closing device according to claim 1, wherein:
the arrangement device comprises a latching member on the distal side of the hand-operated portion, the latching member being configured to pass through the opening penetrating the tissue membrane and latching at least a part of the closure;
the hand-operated portion comprising an actuating member for relatively moving the closure and the latching member;
a trigger configured to trigger the actuating member; and
when the actuating member is triggered by the trigger, the closure and the latching member are relatively moved while the closure is latched to the latching member to deform the deformation portion positioned exterior of the storing member.

15. The tissue closing device according to claim 14, wherein the actuating member is an elastic member, and the trigger includes restriction means for restricting the elastic member to retain the elastic member in an active state, the restriction by the restriction means being releasable by the trigger to trigger the elastic member so that the elastic member is no longer in the active state.

16. The tissue closing device according to claim 15, wherein when the hand-operated part is moved in the proximal direction when the seal portion is in contact with a surface of the tissue membrane farther from a body surface of the tissue membrane, the restriction by the restriction means which retains the elastic member in the active state is canceled by the trigger.

17. The tissue closing device according to claim 15, wherein the arrangement device comprises a retaining member that retains the closure to permit deformation of the deformation portion of the closure.

18. The tissue closing device according to claim 17, wherein when the restriction retaining the elastic member in the active state is canceled, the retaining member is moved in the proximal direction by a restoring force of the elastic member and pulls the closure, in a condition in which the deformation portion of the closure is latched to a distal portion of the latching member, to deform the deformation portion.

19. The tissue closing device according to claim 17, wherein the latching member possesses a lumen, and the retaining member is positioned in the lumen of the latching member.

20. The tissue closing device according to claim 17, wherein:
the hand-operated portion comprises a latching member support portion connected to the latching member and a retaining member support portion supporting the retaining member;
the active state of the elastic member is a contracted state; and
when the restriction for retaining the elastic member in the active state is canceled, the retaining member support portion is moved in the proximal direction relative to the latching member support portion by a restoring force of the elastic member.

21. The tissue closing device according to claim 17, wherein:
the hand-operated portion comprises a retaining member support portion supporting the retaining member;
connecting means connecting the retaining member and the retaining member support portion to each other;
disconnecting means for canceling the connection between the retaining member and the retaining member support portion; and
when the connection between the retaining member and the retaining member support portion is canceled by the disconnecting means, a condition in which the closure is retained by the retaining member is canceled.

22. The tissue closing device according to claim 21, wherein the retaining member is a thread-shaped element having two end portions, and the thread-shaped element passes through the closure and is bent back at a distal portion of the arrangement device so as to retain the closure, and an end portion on at least one side of the thread-shaped element is detachably connected to the retaining member support portion by the connecting means.

23. The tissue closing device according to claim 22, wherein the retaining member support portion comprises a bobbin on which the thread-shaped element is wound in a manner allowing the thread-shaped element to be let off the bobbin.

24. The tissue closing device according to claim 1, wherein the deformation portion is comprised of a porous material.

* * * * *